United States Patent
Lu et al.

(10) Patent No.: US 8,361,474 B2
(45) Date of Patent: Jan. 29, 2013

(54) ANTI-IL-12 ANTIBODY BASED VECTORS, HOST CELLS, AND METHODS OF PRODUCTION AND USES

(75) Inventors: Jin Lu, Boothwyn, PA (US); Thomas Nesspor, Collegeville, PA (US); Bernard Scallon, Wayne, PA (US); Linda Snyder, Pottstown, PA (US)

(73) Assignee: Centocor, Inc., Malvern, PA (US)

( * ) Notice: Subject to any disclaimer, the term of this patent is extended or adjusted under 35 U.S.C. 154(b) by 380 days.

(21) Appl. No.: 12/759,154

(22) Filed: Apr. 13, 2010

(65) Prior Publication Data

US 2010/0216234 A1    Aug. 26, 2010

Related U.S. Application Data

(62) Division of application No. 11/722,281, filed as application No. PCT/US2005/046885 on Dec. 21, 2005, now Pat. No. 7,736,650.

(60) Provisional application No. 60/637,936, filed on Dec. 21, 2004.

(51) Int. Cl.
| | |
|---|---|
| *A61K 39/395* | (2006.01) |
| *C07H 21/02* | (2006.01) |
| *C07H 21/04* | (2006.01) |
| *C12N 15/00* | (2006.01) |
| *C12N 5/00* | (2006.01) |
| *C12N 5/02* | (2006.01) |
| *C12N 5/10* | (2006.01) |
| *C12P 21/04* | (2006.01) |

(52) U.S. Cl. .................. 424/172.1; 536/23.1; 536/23.5; 435/320.1; 435/325; 435/69.6

(58) Field of Classification Search ............... None
See application file for complete search history.

(56) References Cited

U.S. PATENT DOCUMENTS

| | | |
|---|---|---|
| 6,902,734 B2 | 6/2005 | Giles-Komar et al. |
| 6,914,124 B2 | 7/2005 | Bujard et al. |
| 7,063,964 B2 | 6/2006 | Giles-Komar et al. |
| 7,166,285 B2 | 1/2007 | Giles-Komar et al. |
| 7,250,165 B2 | 7/2007 | Heavner et al. |
| 7,279,157 B2 | 10/2007 | Giles-Komar et al. |
| 7,521,206 B2 | 4/2009 | Heavner et al. |
| 7,560,247 B2 | 7/2009 | Giles-Komar et al. |
| 2003/0124123 A1 | 7/2003 | Giles-Komar et al. |
| 2005/0002937 A1 | 1/2005 | Giles-Komar et al. |
| 2005/0112127 A1 | 5/2005 | Giles-Komar et al. |
| 2005/0196838 A1 | 9/2005 | Giles-Komar et al. |
| 2005/0214293 A1 | 9/2005 | Giles-Komar et al. |
| 2005/0261213 A1 | 11/2005 | Branigan et al. |
| 2008/0299133 A1 | 12/2008 | Lu et al. |
| 2009/0202549 A1 | 8/2009 | Giles-Komar et al. |

FOREIGN PATENT DOCUMENTS

| WO | WO 2004/029249 A1 | 4/2004 |
|---|---|---|
| WO | WO 2006/071804 A2 | 7/2006 |

OTHER PUBLICATIONS

Huber, et al., "The Vx genes of the L regions and the repertoire of Vx gene sequences in the human germ line," European Journal of Immunology, 23(11): 2868-2875 (1993).

(Continued)

*Primary Examiner* — Cherie M Stanfield
(74) *Attorney, Agent, or Firm* — Eric Dichter

(57) ABSTRACT

Antibody expression vectors and plasmids can incorporate various antibody gene portions for transcription of the antibody DNA and expression of the antibody in an appropriate host cell. The expression vectors and plasmids have restriction enzyme sites that facilitate ligation of antibody-encoding DNA into the vectors. The vectors incorporate enhancer and promoter sequences that can be varied to interact with transcription factors in the host cell and thereby control transcription of the antibody-encoding DNA. A kit can incorporate these vectors and plasmids.

4 Claims, 2 Drawing Sheets

OTHER PUBLICATIONS

Matys, et al., "TRANSFAC®: Transcriptional regulation, from patterns to profiles," Nucleic Acids Research, 31: 374-378 (2003).

Goessling, et al., "MATCH™—a tool for searching transcription factor binding sites in DNA sequences. Application for the analysis of human chromosomes," German Conference on Bioinformatics 2001 (Abstract).

Henderson, et al, "Transcriptional regulation during B cell development," Annual Review of Immunology, 16: 163-200 (1998).

Henderson, et al., "Lessons in transcriptional regulation learned from studies on immunoglobulin genes," Critical Review in Eukaryotic Gene Expression, 5: 255-280 (1995).

Supplementary European Search Report dated Feb. 1, 2008.

Alberts, et al., Molecular Biolot of the Cell, Fourth Ed., Garland Science, New York 2002, pp. 309, 399 and 400.

SEQUENCE LISTING

<160> NUMBER OF SEQ ID NOS: 56

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
cccaggtgca gctggtg                                                17

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
ctcaggtgca gctggtgg                                               18

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
cccaggtgca gctacag                                                17

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
ccgaggtgca gctggtg                                                17

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
aacctcgagt taacggagg                                              19

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
gcaggaaacc ccacagg                                                17

<210> SEQ ID NO 7
<211> LENGTH: 18
<212> TYPE: DNA

<213> ORGANISM: Artificial Sequence
<220> FEATURE:
<223> OTHER INFORMATION: Primer

<400> SEQUENCE: 7
atccagatga cccagtct                                                18

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
atcgtgttga cacagtctcc a                                            21

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
aatatgcaca aaacttgcac                                              20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
atttgagcct ctaaaggtc                                               19

<210> SEQ ID NO 11
<211> LENGTH: 19490
<212> TYPE: DNA
<213> ORGANISM: Artificial Sequence
<220> FEATURE:
<221> NAME/KEY: misc_feature
<222> LOCATION: (809)
<223> OTHER INFORMATION: Expression plasmid where n can equal a, c, g,
      or t
<220> FEATURE:
<221> NAME/KEY: misc_feature
<222> LOCATION: (995)
<223> OTHER INFORMATION: Expression plasmid where n can equal a, c, g,
      or t
<220> FEATURE:
<221> NAME/KEY: misc_feature
<222> LOCATION: (1046)
<223> OTHER INFORMATION: Expression plasmid where n can equal a, c, g,
      or t
<220> FEATURE:
<221> NAME/KEY: misc_feature
<222> LOCATION: (8220)
<223> OTHER INFORMATION: Expression plasmid where n can equal a, c, g,
      or t
<220> FEATURE:
<221> NAME/KEY: misc_feature
<222> LOCATION: (8283)
<223> OTHER INFORMATION: Expression plasmid where n can equal a, c, g,
      or t
<220> FEATURE:
<221> NAME/KEY: misc_feature
<222> LOCATION: (13101)
<223> OTHER INFORMATION: Expression plasmid where n can equal a, c, g,
      or t

<400> SEQUENCE: 11

```
gctcgacctg caggtcaacg gatccacttc acctgtaggc aaggcacagc acaggggtga      60
gcgaggccac agccctgccc ccgagcccca cccaccccte agggcactga ggccacctct     120
ctgcccccaa ggcccaccca cccgtcagtc cacgcaggcc acagccctgc ccctgaggcc     180
catccggccc ctcatgccac ccaggtgcca tggcctcacc actgcctgct ctgaggcttg     240
gtgatagaga gcagagccag ggcaccaaca gcatgtggac agcacagaag acagcgtcag     300
ggacaggtgg ggacagcgtg ggggacagtg tcagacacag gtgaggacag tgtgggggac     360
agtgtcaggg acaggtggag acagagtgtg aagagtgtt ggggacagtt gaggacagca     420
tggaggagag tgttggggag agatggggac agtgtcaggg agaggtgggg actgtgtgga     480
ggacagcatc agggacaggt ggggacagca tgggggacag tggtgcatac aggaggggac     540
ggtgtggggg acagtgtcag ggattatagg ggacagagtg ggagacagtg tcagggaccg     600
gtggagacca tgtgggggac aggtggggac agcatggggg acaggtgggg acagcatggg     660
ggacagtgtc agggatagga ggggacagga aacagtgggg acattgtcag ggacagggga     720
gatagcatgg gggacagtgt tgggacatg gggacagca tggaggacag tgttgggac     780
tggtggggac agcatggggg acagtgtang agacaggttg ggacaggatg gaggatagtg     840
ttggggacag gtggggacag tgtgggggac agtgtcaggg acaggagggg agatcgtgga     900
gaacagtgtc cgggacaggt ggggacagca tgggggacag tatcagggac aggtggggag     960
agtgtggggg acagtgttgg actggtaggt acagnccggg ggacagcatc gggggacaggt    1020
ggggactgca tggggggacaa tatcanggac aggtggggac atggaggaga gtgttgggga    1080
caggtgggga cagcatgggg gactgtgttg aggacaggtg gggacagctt ggggggacagt    1140
ggtgcatacg ggaggggacg gcgtkgggga cagtgtcagg gattataggg gacagagtgg    1200
gagacagtgt cagggacagg tgggggacagc atggcggaca gtgtcaggga taggagggaa    1260
caggaggaaa cagtggggac attgtcgggg acaggggggga tagcgtgggg gacagtgttg    1320
gggacaggtg gggacagtgt ggaggaaagt tttgggggact ggtggggaca gcatggggga    1380
cagtgtaggg gacaggtggg gacaggaggg gacagcatgg aggatagtgt tgggggacagg    1440
tgggacagt gtgggggaca gtgtcgggga caggaggggga cagcgtgggg gacagtgtca    1500
gggacaggtg gggacagcat ggggggacagt gttgtactgg taggtacagc ctggggggaca    1560
gcattgggga caggtggaga ctgcatgggg gacaatatca gggacaggtg gggacagcat    1620
ggaggagagt gttgggggaca ggtggggaca gcatgggggga cagtgttgag gacaggtggg    1680
gacaaacgtg gggtacagtg tcggagatgg gtggggacag catggaggaa agtgtcgggt    1740
ttaggtaaga caacgtgga ggagagtgtc ggggacaggt ggggacagtg tggggggatat    1800
tgtcacggac aggtggggac agcatgtggg acagggtttc atacaggagg ggacagcatg    1860
ggggacagtg ccaggtactg tagggggacag cgtgggggac agggccagga actatagggg    1920
acagagtggg ggatggtgtc agggacaggt gggggaaagca tgggggacag tgtcagggac    1980
aggtggaaac tgtgggggac agtgttgggg acaaaggggg acaggtgggg gacagtgtt    2040
ggggacagat ggggacagca tggggggacag tgtcgggggac atgtgggggag agcctggggg    2100
acactgttgg acaggtgggg gcagcattgg ggacaatgtc agggacagtt tgtgagagca    2160
tgggggacag cgtcagggac aggtggggac agcctgtggg acagtgtcag agacagtttg    2220
tgacagcatg ggggacaatg tcaaggacag ctggggacaa cgtgcggccg accttgaaga    2280
aggtgacggt ggcactgtag cacacgctta acaggaagag tgtgatgaag atggtgatgg    2340
```

-continued

```
tcgtccacag cccgtccagc tccccgtcct gcgcctccgc acagctctcc tccagttgca   2400
gctctggaca ggaagggggt ggtcagtgct gtgtccccct gggcttgggc ctctgggggt   2460
gattccctct gtggcggggc ccaggatgta gggcccggcc gggatgggcc aacaatgtcc   2520
tgaggtcagc tccccacagc tgcccgccct gggcaccagc tttggccccg ggactcagcc   2580
agacacccgg ccctagatag cgacctggcc ctcagcagga cccgctcccc gtctcccgtg   2640
tccctccctg aggcccagag ggcaggagga tggtgaagcc cacacctcat gtgaccccag   2700
ctgcagggaa gggcggcatt gggaagtggg ccagtgccag ggacgcgacg tggcgtgtgt   2760
tcccctgtgt gtgggggcct gtgtgtgtgt ggcggctgca ggggcacctt gtgagaggag   2820
ggctgggttt gtctgagctg gtcagcatgt ggagaagctg ccgagcggct cgtgggcctt   2880
gaggtgccgc gtggggctcg tgggggcctg tgtccgagga gtgttcacgt gtgcgaggac   2940
cttgctctgg tctgggtgct gtgcggttcg cccgggtgag gctccgtgtg tgaggcgtgc   3000
acgtgtgtgt gtggtggccg tgtggccggc caacctcagt gcggggtttg ttgaacgggt   3060
ctgggctgag tgtgtgtgtg ggcatctgca ccagtctctc cacagggccc gagagtgcat   3120
gtccccagga gtcggttgtg tccccatgtg ggtgcgaggc tgggcagggc tgccaggggt   3180
tagtgccgtg gggtagatg  ggtgagggag ggcctgtccc tacgcgcatg gactaggcat   3240
gcccccgagt gggcatcggg gtcggaggac agggcgctca caggacagga cagtctccta   3300
cagaggcagg ggctgtgtgt ctgtccccag gggctcctag ggcttctcgt ggcccagccc   3360
agggcagctg ctgctggagg gagggccacg ctggcaaatc ccccaccctg ccgagggcag   3420
cccctggctg agccccaccc taggcggccc aggcacacct gcacagcctg ggccagtgtg   3480
gggacagtgg gacccgctct gcctccctca tgccactcag gcctcagact cggcctgacc   3540
cgtggaaaga accatcacag tctcgcaggg gcccagggca gcgctgggtg ctttatttcc   3600
atgctgggcg cccgggaagt atgtacacgg ggtacgtgcc aagcatcctc gcgcgacccc   3660
gagagcccgg ggagcagggg cttgccggcc ctggcactca tttacccgga gacagggaga   3720
ggctcttctg cgtgtagtgg ttgtgcagag cctcatgcat cacggagcat gagaagacgt   3780
tcccctgctg ccacctgctc ttgtccacgg tgagcttgct gtagaggaag aaggagccgt   3840
cggagtccag cacgggaggc gtggtcttgt agttgttctc cggctgccca ttgctctccc   3900
actccacggc gatgtcgctg ggatagaagc ctttgaccag gcaggtcagg ctgacctggt   3960
tcttggtcag ctcatcccgg gatgggggca gggtgtacac ctgtggttct cggggctgcc   4020
ctgtagggac agaggttggt acagcggtca ctctcagggc agagggtggg ccgagccggc   4080
ctctgtccat gtggccctcg caccccacgg gtcccacctt tggctttgga gatggttttc   4140
tcgatggggg ctgggagggc tttgttggag accttgcact tgtactcctt gccattcagc   4200
cagtcctggt gcaggacggt gaggacgctg accacacggt acgtgctgtt gtactgctcc   4260
tcccgcggct ttgtcttggc attatgcacc tccacgccgt ccacgtacca gttgaacttg   4320
acctcagggt cttcgtggct cacgtccacc accacgcatg tgacctcagg ggtccgggag   4380
atcatgaggg tgtccttggg ttttgggggg aagaggaaga ctgacggtcc ccccaggagt   4440
tcaggtgctg aggaagagat ggaggtggac gtgtcagcac ccggctgggg cctgtccctg   4500
gatgcaggct actctagggc acctgtcccg ccttgagctg gagggcgagg cctgggctgg   4560
cttacctggg cacggtgggc atgtgtgagt tttgtcacaa gatttgggct ctgcagagag   4620
aagattggga gttactggaa tctgggagga gagaaggtgt ccgagctgag ggagtggaga   4680
gtttggcctt tggggtgggc ttaggtcagg ggcagggtcc tcccggatat ggctcttggc   4740
```

```
aggtctgagc ccagcacctg cccctttgtg tgcagggcct gggttagggg cacctagcct     4800
gtgcctgccc agagcctggg gaaaaagcca gaagaccctc tccctgagca tgagtggggc     4860
gggcagaggc ctccgggtga agaggcagac ggggcctgcc ttgctgccct ggactggggc     4920
tgcatagccg ggatgcgtcc aggcaggagc gctgagcctg gcttccagca gacaccctcc     4980
ctccctgtgc tggcctctca ccaactctct tgtccacctt ggtgttgctg ggcttgtgat     5040
tcacgttgca gatgtaggtc tgggtgccca agctgctgga gggcacggtc ccacgctgc     5100
tgagggagta gagtcctgag gactgtagga cagccgggaa ggtgtgcacg ccgctggtca     5160
gggcgcctga gttccacgac accgtcaccg gttcggggaa gtagtccttg accaggcagc     5220
ccagggccgc tgtgccccca gaggtgctct tggaggaggg tgccaggggg aagaccgatg     5280
ggcccttggt ggaggctgca agagaggtgg tgccatgtga ccgcggtgtg ggacagagct     5340
gggcccaggg cgcagaggcc cctgggttct taactgtccg cgaggttcag cgtccagtgt     5400
ctgggctcat gggcattggg tgtgcacctg gctggcgcca cctgcctcac cttagcccccc    5460
tccctgcccc aaagccaagg tcaggcctgg cctgcccag aaagcttcag ctgctcgacc     5520
tgcaggcatg caagcttgca ggaccggtgg ccctgtggtg cccttctgca ggcacccctg     5580
cagcctagga ggcggggctc ggcagccagg tcagcgctct gtgcctgccg ggagtcagca     5640
cagtccagtg tctctagctt ggcctcagct ctggccatcg gtgccacctc agggacggct     5700
catgcccatt ggccccactc cagccttta tgggtgcctg gcttgaccag tggacactgt     5760
tctcagatgg cttctggtgg gtccccgag cccctgaag cccctgaccc tgccgctcca     5820
gcatggccct cccctagtga gtgggcctga cttgcccagg gccctggtca tagcctgccc     5880
tctgccctcc aaggcccttt tcttctgtgc agcagagggg ccagacactg catagggtcg     5940
gcgcccttca gccccagggc cccggaaccc cctgccttgg aatatcgccc cgggagcctc     6000
ctcctcagcc tctccctcc tttccctta gccccagtgt gcagcagccc aggtcagggc     6060
cctgagtgcc tggatgcccc ctgcctccca gtgtcctgca ttacttctgg aggctcagtc     6120
accacaacct caccctccca gccctggcct ggccttctcg gccaccagcc cacctcctcc     6180
ctctctccag agcttccccc ggcaaggtcc ctgctgggct caacccaggc cccccagcac     6240
aggtaggagc cttgcacctg cccttggccc tccccaccct gcatggtgcc aggaccccca     6300
ggccacaggg aggcccccatt tctctctgcc gctggcccag tggccctgga gtcccactgc     6360
aggtggggtg tgcccctgac ctctgaggag gctaagtgcc ctgccctcag ccaggccatc     6420
ccctctgctc agcccagggg ccccgctcac caccccttcc cctcacctgc accacaggct     6480
ctggctgact ctgcccaggc cctgaatggg cccctctggc tgccctctgc tgctacactg     6540
tcctgcacca cctccactca gcttcattgt gctggtggcc ctggctcctg gcagcccatc     6600
ttgctccttc tggggcacca gcctcagagg ccttcctgcc cagggtccgc tgggaccagc     6660
cgtgggaccc tcctggtctc aagcacacgt tcccctgca gccacacctg ccctgcctg     6720
agagcccagc cccgagccct ggaacgcctt cccttctcca tcccagctcg cccttgccaa     6780
ctgctcagtg ggatggactc acactcccctt cccggcacca ggaggctgca ctgcactttc     6840
accagccctc agctgtctgt tgccagcaac tacccagctc ctgccaaagt ctaggagctg     6900
agtgatgcct cccaccagcc ctgctcacct gtggctgcct tgccctgagc tctagtgcct     6960
gtccctggt gcaacttagc ccagctcagc tcagctcagc tcaacccagt tcaactcagc     7020
ccagttcagc tcagctcagc ccagttcagc cttgtttagt ctaggtcagt ttaggtcagt    7080
tttgcccatc tgagtccatt tctgaaagct ggatggagtt gtcatggcca gaaatggtca    7140
```

```
gcccaccaga cctgtttgtc tcagctaaag ccatctcatt gccaggttcc tgcacagcca   7200
ggctggcttc catcttttgt ctccctctac ttgataccc agttccctgc agtcctgccc    7260
cagcgccacc tgggttttgg ttccaaagca ttaccaatca ttaccaccct ccactacctg   7320
ggtggaatat ttctttgctg ctttaaagtc attaaaacat cttgagaatg agaccaagaa   7380
tttaggagcc tgtgctgtga taaaaatgag caggtcccct tgctctagaa gtggcagcat   7440
atcttctgca ccaagaggag ggtattgaga tgctcagagc ctccaccttc ccggagcatc   7500
ccctcccttc tgagtctgca gtaaaccct gcctttaaat tccctctaga taacagtcat    7560
cattggaaac aaccaagaaa tgcattttat ctgaatttgc cacttaaaat tctgccattt   7620
accataaatc gctttggaag gcatgggcta ctttcaaggg tgcgatgatg acctacagtc   7680
aatgacttag acaagggcga tgccagtggg gcttggtatg ttctcaagca tcattaccca   7740
tgccatcccc attcagaggt tgtggaacag ctcgtgcgac ctctccttca aatggacttt   7800
agggaaagtt aaatgggagt gacccagaca atggtcactc aaaagactca cataaatgag   7860
tctcctgctc ttcatcaagc aattaagacc agttccccct ctagtggaaa taagacgtta   7920
aatacaaagt tttaagagaa gcaaatgcag cagcggcggc tgcctgtctc ttaccatgtc   7980
gggcgcctgg tcactgcgag ccttgcaaag ctttggcatg gaatcattcc tccaagtcca   8040
ttaacaaggg ctggggcctg agcagccagt cggcccggca gcagaagcca cgcatcccag   8100
ctctgggtag tccggggaga cccaaagccc aggccgggcc tggcagccac cctcccagag   8160
cctccgctag gccagtcctg ctgacgccgc atcggtgatt cggaacagaa tctgtccttn   8220
taaggtgtct ccacagtcct gtcttcagca ctatctgatt gagttttctc ttatgccacc   8280
aantaacatg cttaactgaa ataattcagg ataatgatgc acattttacc taaaacttat   8340
cctaaagtga gtagttgaaa agggtcttga aaaatactaa aatgaaggcc actctatcag   8400
aatatcaaag tgtttctcct taatcacaaa gagaaaacga gttaacctaa aaagattgtg   8460
aacacagtca ttatgaaaat aatgctctga ggtatcgaaa aagtatttga gattagttat   8520
cacatgaagg gataacaagc taatttaaaa aacttttga atacagtcat aaactctccc    8580
taagactgtt taatttctta aacatcttac tttaaaaatg aatgcagttt agaagttgat   8640
atgctgtttg cacaaactag cagttgataa gctaagattg gaaatgaaat tcagatagtt   8700
aaaaaaagcc ttttcagttt cggtcagcct cgccttattt tagaaacgca aattgtccag   8760
gtgttgtttt gctcagtaga gcactttcag atctgggcct gggcaaaacc acctcttcac   8820
aaccagaagt gataaattta ccaattgtgt ttttttgctt cctaaaatag actctcgcgg   8880
tgacctgctt cctgccacct gctgtgggtg ccggagaccc ccatgcagcc atcttgactc   8940
taattcatca tctgcttcca gcttcgctca ttaattaaa aaaataaact tgatttatga    9000
tggtcaaaac gcagtcccgc atcggggccg acagcactgt gctagtattt cttagctgag   9060
cttgctttgg cctcaattcc agacacatat cactcatggg tgttaatcaa atgataagaa   9120
tttcaaatac ttggacagtt aaaaaaatta atatacttga aaatctctca cattttttaag  9180
tcataatttt cttaaccatt tttctcagaa gccacttcaa acatatcctg tcttttaaca   9240
gtaagcatgc ctcctaagat aaacaatcct tttctcatgg aaaccagctt caaggcactg   9300
aggtcctgga gcctccctaa gccctgtca ggacggcagc cactgttct gggctacccc     9360
tgccccccaac cctgctctca tcaagaccgg ggctacgcgt ccctcctggc tggattcacc  9420
cactccgaca gttctctttc cagccaaaaa agaatctaag atgcaggttg acacacagcg   9480
cacctcataa ttctaaagaa aatatttcac gattcgttgc tgtgcagcga tcttgcagtc   9540
```

```
ctacagacac cgctcctgag acacattcct cagccatcac aaagacccct ggtttgttca    9600
ggcatttcgc ccaaatgtgg cgccccaagc ccccaggctc agtgactcca tcagacgcac    9660
ccaacctgag tcccatttc  caaaggcatc ggaaaatcca cagaggctcc cagatcctca    9720
aggcaccca  gtgcccgtcc cctcctggcc agtccgccca ggtcccctcg gaacatgccc    9780
cgaggaccaa cctgcaatga tcaggaaacc ccacaggcag tagcagaaaa caaaggccct    9840
agaatggcaa ctgactgtcc gtggccctgt cctgcccttc tcatggaatc ctctgttggc    9900
ctcccacgta ccccacattt tggcctgacc cctcagaagc cagaccactg tcggcctggg    9960
aagcccaact gcaagcagac ggcttctaag tcactcccag gagtccaaaa accccggggg   10020
gcacccgtcc cagagagcgg gtgccttgga gcgggacaga gtcccaccac gcaatcatca   10080
cgacagcccc tgagaatgct ccaggtgaag cggagagagg tctccccaga ccagccgaag   10140
gagccccca  cctgccgaca tctgtggccg ggcttgggga ggacaggctg ggttcccatt   10200
cgacgggtcc ctctccccgg cttcttttcc tgacctccaa aatgactcca agactctgac   10260
cctgagaccc tggcaagttg agtctcccta agtggacgca gagaggggt  ggtgaggact   10320
cacctgagga gacggtgacc agggttccct ggccctaggg gtcgaaccag atgtcacatc   10380
gtgacaacaa agccaggacc ccaggcaaga attggcgccc cgtatgtccc tgggacccac   10440
tcagattgaa cccggggagg gcccggggtt ggtgggcact ggaccccaga ggcctagggt   10500
ggccctggcc acagagagag gcgtcctatt gggctcagga ggaaggagaa ggtggagccc   10560
gctattgtct cagggcatcc tcctgagtcc cccaggttgc tccggggctc ccttggcagg   10620
agacgcagca ccctcatgtc cccccaaaaa tgcaacaaaa tccttcagac ttaaagtagg   10680
agagaggttg tgaggactca catgaggaga cggtgaccag ggttccctgg ccccagaagt   10740
caaagtaacc ctgtccagga cgtcttctcg cacagtaata catggcggtg tccgaggcct   10800
tcaggctgtt ccactgcaag taggcggtag tgatggactt gtcgactgac atggtgacct   10860
ggccttggaa ggacggacta tatctgatat cagagtcaac aggagacatg attcctatcc   10920
agtccaggcc tttcccgggc atctggcgca cccagccgag ccagtaggtg gtaaagctgt   10980
agccagaacc cttacaggag atcttcagag actccccggg cttttcacc  tctgctccag   11040
actgcaccag ctgcacctcg gcacagactc ctgtggggga gacacaaaat ttgaatcagg   11100
ggctcctttc cacccgttct cctctgtgac ctcaagacct cggcaggact gaccttggag   11160
aacagccagg aggaggccga ggatggcggt tgaccccatg atggtggagg acagaaaatg   11220
aagccctgag atcccagctg ggcagtgagg gagactcact gtggaggga  gccctgggtt   11280
taagtgggga ggccccact  tgcatttgca tagttgtcac cctgccctga agggaggagt   11340
ctacagcgtt tataacccag aacctcaaat gcagaaaaag gctggcctga gcctcctggg   11400
aggggcagag taaggtctca ataattcctt acaccctgct attgtccctc tccactcttt   11460
tacatgtttc ttcgagaccc ataccagggc ctcccttctt ccacccttct ctgtgaccct   11520
gtgaaggtga taaatctagt tgaaactatg tgtgttaaaa aaatgagaa  atagtgccag   11580
gaaaggccat gaagagaaaa ttcaaatgca cttatgcctg ataacaagaa ctactaaaaa   11640
aactactgtc tattccctgg caatttcgtg tgagttggac tacggcctgg gcatcaagca   11700
agggcaggac cacctcagga cctcaacagt cctcaagatg attaacttgc cagaccttca   11760
cccatgcaaa atcgcacatt tttcctggcc atttttgtctt ctagattttt acactctgcc   11820
aattcaacat gaataggaa  tatttgttta ggtctctgac ttgctgatgg acctgaaggg   11880
atgcccattg ctgcacccaa ctcctggtag tgctgtttta agtcctttgt gtcaacccca   11940
```

```
gcaccttctt gtttagttct ttcatttttt aacatttatt ttatgatatc cacattgctt    12000
ggaggaggcc cttaactatc cccttgtct gccccatttt tttgtgaagc actctcattt     12060
cattagcacc taaaagatcc agagaaaaag ccaaagcaac acaaactaca caagttctga    12120
aactatacag gatctgatat ccagtgcacc agggaagctg tctcatcaag aacatcctac    12180
ttgaggttgg gatcagctac gtctgtcata tgtctgttgt gagctgtggg tccagcatcc    12240
tcccaaacat tctcctctca tctgcagcac acgaagccag agaagctgct acgtcagtca    12300
ctctcatagt ccattggcta actttgttca caatccgatg atataaatta atgatatcaa    12360
tcatatcaca aaatgatgcc actttccatg ctgtcctcct tgttatagtt gtctagtgga    12420
ttcctctccc cagcccaaac tctgggctac cttctgtgtc actcttatgt gttgtgtgtt    12480
gtttctggac aactgtaccc tttggtggtg aatgggagtc tagcagcctc ggctcacagg    12540
gcacactgca gggctggatg tgcatctttt tactattatt ttagctatca cagatatgaa    12600
ttgcatattc gggttgttcc tcattatttt tacttttcct ttttcaggga acaactccta    12660
ggaagctgta tctgttgttt ctaaattcca tggattactt tcacttcctg ctccttattg    12720
gagtgtacat gccatctcat gccatatgat tctgtagcca tctgggcatt gaatgtcttt    12780
tatcccgcac tttctcatcc tttgatgtta taaaaaatcc tctagccatg cgtcagcaat    12840
caggaacttt ctagcattct ccaactctga tgtaattgtg ttgagtgtcc caagaccatc    12900
ctcaggcccc ttaatcagta caaataaagg acacaagaaa agctgttatt ctcatgggtg    12960
cagctttatt atagcgaatg aatatgaatt aaaatgagca aaggcaccag ggagaaggcc    13020
ctgagaatcc aggcatgagc tcccaggtgt tctttcctg aggagtctct tgtccccagt     13080
tctcccagca gtgatgcatg ncaacatgtg tgaagcattg tccaccaggg aagctcacct    13140
gagtgcttgt gcccagggct gtttattggg cccatcacag atgtgtgtga cacctgcaca    13200
attgacctcc agtgctcaga cgccggcctc ttgagcacta ataggcattc accataagtc    13260
attatgaaaa cagctagtat agcgtgcacc caggctacac acacagagac acagacaaac    13320
acaaacaaaa atacatttta actaataaaa taatcacaat actaagagag ataagaggaa    13380
tgttttggaa gtgatttcta tggttatgac cttgatgatg gggataactt tgcagatgta    13440
tacttactcc aaactcaatg agttaagtat gttaaataat gtgtagtttt acagatgtaa    13500
accttatctt aatcaagtgg tttaataata ctaccaggag gagtatgcca aaaaggcaga    13560
tatcatctcc caggagctga atatgggcct agcttgagaa agcacttttt caggaatgtt    13620
cagggtttgc acaacccaag actgctcggt aaatcctttc ctgtacacaa gtccaggtga    13680
gatggaaaca ggctgttgga ataaaggca aagctcagaa gaaaagagag aggaagtggt     13740
ggacaaggta tgaccccatg tagggttagt gtggatggga ggtgctgctg agagcctgtg    13800
gatggagaag aatgtggacc aggggcagga ggaaaaaagg cagaggaggg gttcttcctg    13860
agccaaagca gatgtttcac ggagagtgtg ggcaggggca tgcctgcagg tcgagtgctt    13920
tctacataag ttatgggacc atagcagagt ttcccaactc ttctgagtca cttctgatc     13980 ctttagtgtc ttgcccacct ctggtcagta actccttcga tctcccctta attaattaaa    14040
ctctgttgtc agcccaattg ccaccagcag ctagttttcc ttaaagggtg tagtgtgtgt    14100
tggtatgggc agagcattcc actagagcca tgagaaaatc ggagttctac aaggacacag    14160
ccatggataa agacaattcc tactcaagct agctgaagaa ctgtaaattt gaaagccagt    14220
gtctgagcgc cctctactgg aagcaatggc acattactcc cagcatcatt ttccagcaca    14280
aaagacctaa attgttgaga tgagacattg gcttagcatt ttcttgactc tcactttcag    14340
```

```
tttcttccag aactcctgat gttgacacaa gacatgacat atgaaggtgt aagttaatta    14400
aaagacgctt tccagcatcc aagatgaggg aaaggtgaga aatactgaga ggctgtgtaa    14460
aatggagtcg tttcttgttg catgctaagg ataaatagca tccttgccga ttcttgccag    14520
cctgcccaga aaaatgtgag ttctagcagc agtttctcag ttatcactga cagaacctga    14580
ttgcttaatg atttatagct ttattacata gtggccaaga gcaagcccct ctggtaagtc    14640
acttcttcaa tttggtgaca agaaaccagc catcaggaat gatgtatttc cttgtaagtt    14700
ccttgagaaa tacgagattt ttcctctgtg tgcctgtgtg tggtgtttat gcccgtgtgt    14760
gtgtgtgtgt gtgtgtgtgt gtatgtgtgt atgtgtatgt gtgtgtgtgt ttgtatgtgt    14820
gtgtgtatgt atgtgtgtgt gtgtatctct agtccctgct ttttctttct actgactttg    14880
cagttgtcct gattatttgt tggtttacta cagtactggg gatccgttga cctgcaggtc    14940
gaccggatcc agacatgata agatacattg atgagtttgg acaaaccaca actagaatgc    15000
agtgaaaaaa atgctttatt tgtgaaattt gtgatgctat tgctttattt gtaaccatta    15060
taagctgcaa taaacaagtt aacaacaaca attgcattca ttttatgttt caggttcagg    15120
gggaggtgtg ggaggttttt taaagcaagt aaaacctcta caaatgtggt atggctgatt    15180
atgatctcta gtcaaggcac tatacatcaa atattcctta ttaaccccctt tacaaattaa    15240 aaagctaaag gtacacaatt tttgagcata gttattaata gcagacactc tatgcctgtg    15300
tggagtaaga aaaaacagta tgttatgatt ataactgtta tgcctactta taaaggttac    15360
agaatatttt tccataattt tcttgtatag cagtgcagct ttttcctttg tggtgtaaat    15420
agcaaagcaa gcaagagttc tattactaaa cacagcatga ctcaaaaaac ttagcaattc    15480
tgaaggaaag tccttggggt cttctacctt tctcttctttt tttggaggag tagaatgttg    15540
agagtcagca gtagcctcat catcactaga tggcatttct tctgagcaaa acaggttttc    15600
ctcattaaag gcattccacc actgctccca ttcatcagtt ccataggttg gaatctaaaa    15660
tacacaaaca attagaatca gtagtttaac acattataca cttaaaaatt ttatatttac    15720
cttagagctt taaatctctg taggtagttt gtccaattat gtcacaccac agaagtaagg    15780
ttccttcaca aagatccggg gcccactcat aaatccagtt gccgccacgg tagccaatca    15840
ccgtatcgta taaatcatcg tcggtacgtt cggcatcgct catcacaata cgtgcctgga    15900
cgtcgaggat ttcgcgtggg tcaatgccgc gccagatcca catcagacgg ttaatcatgc    15960
gataccagtg agggatggtt ttaccatcaa gggccgactg cacaggcggt tgtgcgccgt    16020
gattaaagcg gcggactagc gtcgaggttt caggatgttt aaagcggggt ttgaacaggg    16080
tttcgctcag gtttgcctgt gtcatggatg cagcctccag aatacttact ggaaactatt    16140
gtaacccgcc tgaagttaaa aagaacaacg cccggcagtg ccaggcgttg aaaagattag    16200
cgaccggaga ttggcgggac gaatacgacg cccatatccc acggctgttc aatccaggta    16260
tcttgcggga tatcaacaac atagtcatca accagcggac gaccagccgg ttttgcgaag    16320
atggtgacaa agtgcgcttt tggatacatt tcacgaatcg caaccgcagt accaccggta    16380
tccaccaggt catcaataac gatgaagcct tcgccatcgc cttctgcgcg tttcagcact    16440
ttaagctcgc gctggttgtc gtgatcgtag ctggaaatac aaacggtatc gacatgacga    16500
atacccagtt cacgcgccag taacgcaccc ggtaccagac cgccacggct tacggcaata    16560
atgcctttcc attgttcaga aggcatcagt cggcttgcga gtttacgtgc atggatctgc    16620
aacatgtccc aggtgacgat gtatttttcg ctcatgtgaa gtgtcccagc ctgtttatct    16680
acggcttaaa aagtgttcga ggggaaaata ggttgcgcga gattatagag atctggcgca    16740
```

```
ctaaaaacca gtatttcaca tgagtccgcg tcttttacg cactgcctct ccctgacgcg      16800
ggataaagtg gtattctcaa acatatctcg caagcctgtc ttgtgtccaa gctagctttt     16860
tgcaaaagcc taggcctcca aaaaagcctc ctcactactt ctggaatagc tcagaggccg     16920
aggcggcctc ggcctctgca taaataaaaa aaattagtca gccatggggc ggagaatggg     16980
cggaactggg cggagttagg ggcgggatgg gcggagttag gggcgggact atggttgctg     17040
actaattgag atgcatgctt tgcatacttc tgcctgctgg ggagcctggt tgctgactaa     17100
ttgagatgca tgctttgcat acttctgcct gctggggagc ctgggactt tccacaccct      17160 aactgacaca cattccacag ctgcctcgcg cgtttcggtg atgacggtga aaacctctga     17220
cacatgcagc tcccggagac ggtcacagct tgtctgtaag cggatgccgg gagcagacaa     17280
gcccgtcagg gcgcgtcagc gggtgttggc gggtgtcggg gcgcagccat gacccagtca     17340
cgtagcgata gcggagtgta tactggctta actatgcggc atcagagcag attgtactga     17400
gagtgcacca tatgcggtgt gaaataccgc acagatgcgt aaggagaaaa taccgcatca     17460
ggcgctcttc cgcttcctcg ctcactgact cgctgcgctc ggtcgttcgg ctgcggcgag     17520
cggtatcagc tcactcaaag gcggtaatac ggttatccac agaatcaggg gataacgcag     17580
gaaagaacat gtgagcaaaa ggccagcaaa aggccaggaa ccgtaaaaag gccgcgttgc     17640
tggcgttttt ccataggctc cgcccccctg acgagcatca caaaaatcga cgctcaagtc     17700
agaggtggcg aaacccgaca ggactataaa gataccaggc gtttccccct ggaagctccc     17760
tcgtgcgctc tcctgttccg accctgccgc ttaccggata cctgtccgcc tttctccctt     17820
cgggaagcgt ggcgctttct catagctcac gctgtaggta tctcagttcg gtgtaggtcg     17880
ttcgctccaa gctgggctgt gtgcacgaac cccccgttca gcccgaccgc tgcgccttat     17940
ccggtaacta tcgtcttgag tccaacccgg taagacacga cttatcgcca ctggcagcag     18000
ccactggtaa caggattagc agagcgaggt atgtaggcgg tgctacagag ttcttgaagt     18060
ggtggcctaa ctacggctac actagaagga cagtatttgg tatctgcgct ctgctgaagc     18120
cagttacctt cggaaaaaga gttggtagct cttgatccgg caaacaaacc accgctggta     18180
gcggtggttt ttttgtttgc aagcagcaga ttacgcgcag aaaaaaagga tctcaagaag     18240
atcctttgat cttttctacg ggtctgacg ctcagtggaa cgaaaactca cgttaaggga     18300
ttttggtcat gagattatca aaaaggatct tcacctagat ccttttaaat taaaaatgaa     18360
gttttaaatc aatctaaagt atatatgagt aaacttggtc tgacagttac caatgcttaa     18420
tcagtgaggc acctatctca gcgatctgtc tatttcgttc atccatagtt gcctgactcc     18480
ccgtcgtgta gataactacg atacgggagg gcttaccatc tggccccagt gctgcaatga     18540
taccgcgaga cccacgctca ccggctccag atttatcagc aataaaccag ccagccgaa      18600 gggccgagcg cagaagtggt cctgcaactt tatccgcctc catccagtct attaattgtt     18660
gccgggaagc tagagtaagt agttcgccag ttaatagttt cgcaacgtt gttgccattg       18720 ctgcaggcat cgtggtgtca cgctcgtcgt ttggtatggc ttcattcagc tccggttccc     18780
aacgatcaag gcgagttaca tgatcccca tgttgtgcaa aaaagcggtt agctccttcg      18840
gtcctccgat cgttgtcaga agtaagttgg ccgcagtgtt atcactcatg gttatggcag     18900
cactgcataa ttctcttact gtcatgccat ccgtaagatg cttttctgtg actggtgagt     18960
actcaaccaa gtcattctga gaatagtgta tgcggcgacc gagttgctct tgcccggcgt     19020
caacacggga taataccgcg ccacatagca gaactttaaa agtgctcatc attggaaaac     19080
gttcttcggg gcgaaaactc tcaaggatct taccgctgtt gagatccagt tcgatgtaac     19140
```

-continued

```
ccactcgtgc acccaactga tcttcagcat cttttacttt caccagcgtt tctgggtgag      19200
caaaaacagg aaggcaaaat gccgcaaaaa agggaataag ggcgacacgg aaatgttgaa      19260
tactcatact cttccttttt caatattatt gaagcattta tcagggttat tgtctcatga      19320
gcggatacat atttgaatgt atttagaaaa ataaacaaat aggggttccg cgcacatttc      19380
cccgaaaagt gccacctgac gtctaagaaa ccattattat catgacatta acctataaaa      19440
ataggcgtat cacgaggccc tttcgtcttc aagaagaatt ccaagctatt                 19490
```

<210> SEQ ID NO 12
<211> LENGTH: 19412
<212> TYPE: DNA
<213> ORGANISM: Artificial Sequence
<220> FEATURE:
<221> NAME/KEY: misc_feature
<222> LOCATION: (790)
<223> OTHER INFORMATION: Expression plasmid where n can equal a, c, g, or t
<220> FEATURE:
<221> NAME/KEY: misc_feature
<222> LOCATION: (13753)
<223> OTHER INFORMATION: Expression plasmid where n can equal a, c, g, or t

<400> SEQUENCE: 12

```
ttccaagcta tgctcgacct gcaggtcaac ggatccacat atataattta gaagttttca        60
ctagccatgt tataaaagta aaagaaatc tgtgcaatca attttaataa tattttgtt        120 tgcacacaag atatcaggg taatctcaac atgtaatcat ataaaatatt aatattttac       180
acgtattttt tgtacaaaat gttaaaaatt ggatgtgttt ttacacgtat agcccatctt       240
agtatggact ggccttatct ccagagctca ataactctgt gtggctagtg gcaggatatt       300
ggatatcaag tctagaacat acgtgaatta attcaaggtt caagcacatt aaggctgaaa       360
gagttatgac tgaagaacaa gttcaaggag gaaatcaaac aatagccaaa tttcactgag       420
ctactccttc cattactaat gataacaaat atttatagat cccttagtat atactaggcc       480
tgatgcttag aactttatat gaactgtttc atttaatcct cacagcaatc ttacaagtaa       540
gacctccacc cccttttcaga tgagaaaact gaagcacaaa agtgcagtaa cttgctatta      600
tgacttgtga gcatattttc ccaggcaatt atatgcacag gatgatgtag gtaaagcagc       660
ccaataattt attcactata tttctccatg ctcatggtaa ggactgactt gatccctggt       720
ggtcacccac ttgtgctccc tcagtgaggg aagggctgca gagcccctgg cccgtgtcct       780
agtgactcan gcttgggatc tccagcagct gctatggttg acaatttagt ttagtaaaat       840
gttagatcct accctgataa ctgttataaa aaatcctcct tccccttccc cagcacaggt       900
acccagccca aggggcactt tctatggaaa gatgaaaaga actgacatgg acttgagctc       960 actggggtg caggtttcaa gaaagaacaa agagagctgt taggttgaag agacgcagtt       1020
gaagagttaa gtcttggaat tgttaatacc tggaacaagg cacggtgtga aaagacaaag      1080
aaacacacaa acatcaatct gtcctcctct tttctctttc tgtttcattt cttatcctcc      1140
atcagtcaga ctttgcttcc tctttctcct ccttcacctc ctcctccctg cccttcccaa      1200
tttctttcta tcttccattt attgttcttc caaaattcgt atactcatcc tctcttctcc      1260
cttctctttt tctccaaaat aatatgttca acttactgac ttgctcaggg acttgtgggg      1320
gcgaatgtat tagcaccaaa cctaggaaac atggcgaatt ctaaaaactt gttctcatag      1380
aaaaaagagt taaaaataga aagctacagt ccagttttga agccacagaa gacctcactc      1440
tgatgtatag acattagagt cagaaaaaga ctttgaaaag accagtgaag ctccttgtcc      1500
```

-continued

```
cacagacagt gtgagggagg gacaagggga attgtgtgcc aagcgtact tgggatggtg      1560 taggtggctg ataagagtgt cagtggaggt ggtggttagc atttggagtg ccccaatctt      1620
gtgacactaa acatttattg ttatactaac cccactgcca actaccagga agttttcatt      1680
tttcttactg tgtcttagtc tccatggcat ctataaactg ttttccccca atgtccaggc      1740
atcattcctc tcccacagtt gatgtctggc tctgtgccat gggtgtgggc ctgcctcttc      1800
tctctcagaa tgactgctgt ttcatgcttg gtgagccacg cagtatgcca agctgctgtc      1860
tctgacctgg agaaaggata cccatcctac acaggtggg gcatatcatg ggatggcctt       1920
cctggttttc cttggcagac acattttct cactttttt tttctctcct cccttctctt        1980
tttccctccc tctttgattt cttctctttt ccttttcttt ctcttgcctc acttctgccc      2040
tagatctacc atgggaccca gggagctttg gagccatgca acccacagtg tgctaagctt      2100
tttactcatg ctatttcttt taatcttcac aattctttac ctatcaggca ttaccatcag      2160
atctgcacct tacaggtgag aaagggaggc ccacaccgat taagaaatgt gctcagggcc      2220
acacagcctg tacatgtcag agtaagggca ttctcatgcc aaggttcatt ttcagagcca      2280
aaagcatacc acgtctcagg agaagcaggc tagatctctt gtctgcttgg cttttaactc      2340
atgctgacct gaactttctg gatttgagta actctcagac ctgtggagcc cgatttctgt      2400
gagtggattt tgccagccac ctggggaggt gaacccttgc tggggtatgg ctcattagtg      2460
tagaagggag ttccttcaga ggtacgctgt cttctcggcc atccccattg tagtagtttc      2520
ttgggtctgc cctaacaaag taccacaaac taagagccgt aaaacaacag aagtttattc      2580
tgtcataggt ctggagacag aaatctgaat tcaaggcaca ggcagagtta gtgtcttctg      2640
caggttctcg gggagaaacc atcccacacc tctccagctt ctggtggctc ccagcaatcc      2700
ttggtgctct ttggctctca gctgcatccc tctggtctct gcctccttgg tcatgtggct      2760
ttcttcctat gtgtcactgc atctccaatc tccttcttct tataaggaca ccagtcattg      2820
gatttagggc ccactcggat ccagcataaa aaaaaagttt aaaaaaatta tttggaaata      2880
attatagatt cacagaaagt agcaaagaca ggatataaag cacagaggtc tgatgtgtcc      2940
tgcacccagt ttctcctgtt ggttacttct tacgtaatta cagtacgata ttaaaaccaa      3000
gaatttgaca ttgataaaat aagtgtgtac agttctatgt cattttatca catgtctaga      3060
tgcctgcaac taccactgca atcaagatac agatttatcc catgatcaca aagatctccc      3120
tttatagttt cgcctactct tctttctcca ccaccctaac ccctggcaac cagaatctgt      3180
tctctatccc tataattttg tcacttcaac aatgttacgt aaaaggaatc acatggtatg      3240 tgacccttc agattggctt ttttcactca gtagaaagtc cttcagaatc actccagttc       3300
tctgtatcaa cacttcgttc cttttttattg cctcatagca ttctatggca tggatatatt     3360
acaatttgtt aggctagttg cctattgagg gatgggttgg ctctttctag ctttggctac      3420
aacaaataaa gctgctgtga acaatcatgt atgggttctg tgtggacata agttttatt       3480 tcctgggggt aaattcccaa ggagtacaat tcctgggtca tatggtaggt gtcttttgtt      3540 tagttttttca agaaactgac aactattttc tagagtagct ataccctttt atattcccac     3600
cagcaatata tgaatgatcc atttttcaccg catcctcaca aacatttcag tatgacctaa     3660
ttttgacttg attacctctg caaagaccct atttccaaat aaagtcacat ttatgtgacc      3720
catttatgag taccaagagc aaggagttga gcatacccttt ttgaaggaca caattccacc    3780
tgcagcacct gtcttcactt gcttaggtta tgggtgggtt tcacttcaga gtgttatctt     3840
ctgagaagaa ggtttgaatt cataactgga ttatgcctgc ctttgattgt tcaatttggc     3900
```

```
cccagggat gagtgagcaa gttcatgtca ttggaaggga cattactgag tctcacccct    3960
actcaaacct ccaaagtttg aaagatttga tactcatcaa cattctcaag aggcagaagg    4020
gcaaggtgct tccttatgta gtttctccat gactgtcctt ccccacttc ccagtactga    4080
ctggaaagaa aaacaaagca ggacaaaggg attgtcagtc atttgaggga agggatgctg    4140
tgttagttac tcctgaaccc cttcagagtg taggcagaga gaggtactta gaaaggtgtg    4200
ttggatggat gagtagctga gaggggcagg gccagagtgc cccatagaat gaggaagagt    4260
cctcatttac atgtgccctt ccccttccc aaacatgtga gtgttcatac atgggtttcc    4320
agtgtctggg caaggttaat tctgtcctct gtccccttgc tgaaggtctg tttcatttaa    4380
tttctatgta tgtgtgctcc tagctagcca acagggcac agatgccagg aaaatagcag    4440
gcctgttgtt ttgttgagca ccttgagccc tggaaggcag actcattcag ggctcaagag    4500
ggcaggatta ggcaggtagc tatttgatcc caggccccc cacttaccag ctgcgtggtc    4560
ttgacctatt acttattcct cttctatcta ttaactgggt ataagatgtt ctttatgtga    4620
agttattttg aagcataatg tgtatacaga acagtgcaca gatcataact gcacaacccc    4680
acacgaggaa cagaacatta ccaagacccc agaagcccct tcttgtcttc tcccaggcac    4740
taactcgccc acccccagct aagagtaatt ccatccaaa tttctaactt tattttacc    4800
tggttttgaa cttatatagg atgaaaacat acagaacata tcttttgcat tgagtttctc    4860
ttatgtaaca ttattttat gagattcatc tgtgtgagta ggtatagttg tagcttgtta    4920
attctcctca ttgggtattc taatgtataa acataccaca gtttaataac tcattctatt    4980
gttggacaat cgggctattt ccaattttg gcttttgtaa ataaagctgc tttgaacatt    5040
cttgcatagt tttttggtgg gtggggacac tcagtcatct agaagtggga ttgctgagtt    5100
atagaatata tttgtctctc agctttatag aacctttgca acatttaat gaatgttttt    5160
aatctcacag tatagtgtgg attaaattag gttgtggaaa gtactcaata cggcccttgg    5220
cagacaggag tccctcagta cctgtttaaa aatgtaaata aggcatgaca ttccattaag    5280
tctaagtacc atgatgaact taaacatttc cctattgttt gtttatttaa ttgcttttat    5340
tgtgttgtta tttatatca tgttgcaatg aatgattctc tttatagcag gtttcttctt    5400
ttgaaaaatt tgctttggtt gattctcagg gaattgaatc aaaggatata tgactgtaag    5460
acctgtcacc cttaaaaagg actatgaggg cttgctgagg aggggaaaac aaggaagcaa    5520
gtctctccta ccatggccca ggggactgtg aggacagaag gcttgtgggt ttgagggagg    5580
actgtcttgc agaggatgat agggtaaaat agaatgaagg atgatttta taaatggtta    5640
tgcgccttag gatgactaca tatttagtcc cttataagag aaattgagta gttggtaaaa    5700
caacagataa taattattaa atgaggaaag agagaaacca caggtgcaaa gattcacttt    5760
atttattcat tctcctccaa cattagcata attaaagcca aggaggagga gggggtgag    5820
gtgaaagatg agctggagga ccgcaatagg ggtaggtccc ctgtggaaaa agggtcagag    5880
gccaaaggat gggagggggt caggctggaa ctgaggagca ggtgggggca cttctccctc    5940
taacactctc ccctgttgaa gctctttgtg acgggcgagc tcaggccctg atgggtgact    6000
tcgcaggcgt agactttgtg tttctcgtag tctgctttgc tcagcgtcag ggtgctgctg    6060
aggctgtagg tgctgtcctt gctgtcctgc tctgtgacac tctcctggga gttacccgat    6120
tggagggcgt tatccacctt ccactgtact ttggcctctc tgggatagaa gttattcagc    6180
aggcacacaa cagaggcagt tccagatttc aactgtctcat cagatggcgg gaagatgaag    6240
acagatggtg cagccacagt tcctgaggaa agaagcaaac aggatggtgt ttaagtaaca    6300
```

```
aagttctgcc cttgggtgtg ttgtttgcgg ataatcacag ggcatgttag ggacagacag    6360
aaaacagcat gcttatccca gataattata gcaaggagac caagaagcgt atttaaaatc    6420
ttgatgtttt gagtttcttc ctagcttccc cctattcctt aataaagttc taaattgttt    6480
tgttggagct ctttgcagcc attctgaggg ctttgcatgc ttttctgacc ttgcagtaaa    6540
ctcaatgctt taggcaaaga atggccacgt catccgaccc cctcagagtt tagaattcag    6600
aacaggtctg aagaagacca ggcagcggct gagtcaagga aagcctccgt ccgcttttat    6660
ttcccctgtg cctcttccag gactgtgctg ggataacagg ctcccggggg ttactttggc    6720
tgggctgggc taaaacctcc ctgcagagca ggccctgagc cctgcctctg cgcctgggtg    6780
gtgtcagccc ctccaccttc tgactgttcc agcaactctc taagccctcc caaaggcctc    6840
aaggcctgta accatatgca gcaattttca gccataccag gagaggtcaa ctgtaatctt    6900
ggccacctgc ctaagaggaa gtggctagct tcacttctga ccctcagcaa ctgccaggtg    6960
gcctcttgga atccccctc tgggggattc cacccgttgg gtgggagagc agtagttaaa    7020
atgtaaaata agaatctttt gctgggagaa gtcaacagat agggagaagt cagctgataa    7080
cagaaatagt tttttttttt tttaaaacta acttcactgt taaccaagca gttcaacatg    7140
aaagactgaa tctcttatgt ttaatatttt cttctctttt aatcttcata actaattttt    7200
ttcagataat tgtataaaat aaccatggta gcaaaataat gtgatcactg gaaaataagc    7260
agggaaaaac atgctatgaa gatactccta tctgggtgaa ttcttgatag ctttacattt    7320
ttcatctggc atttaaacat taaacagtta atgtatttga catgaaaatt atttcaagtt    7380
atcttattag ttttaataga gtttaaaaag tgtttaaaag agttttcaaa aggctctaaa    7440
atcattttga aatagtttaa aacagttttg aatcgttgta agttagtttt aatagagctt    7500
taaaaaggcc ctaaaatagt cctatcaagt tgttgcagac caaaataatc tccttaaata    7560
tcacttttga gatcagctgg ggtaaacgac agcaacacaa tgacaaatca ttaaactatt    7620
ttagagatta tgaaattaaa atactcagat taaaattttc ctatcacaga attaaggtac    7680
tggaaaatat gtttaagttt ttattaatcc attgctatag gtttagatat tttgtacaac    7740
tgaaataaaa tcacacactg gcagctacat ttttgaaagt taaaaacatg gtcacgaata    7800
tatcttattt taaaatcagt taatatacct taatggtatt taatgccaaa ttcaaagtga    7860
attgatcaag ccctcagtgg ccaggtcatg ggtgtgattt ttactctgaa agaattacat    7920
atttctttct ttttggttga gcttttgtta tttaaataca tttgatgaga ggatattgaa    7980
ataattaaat agcactgaaa aaaaaaagct ttaaattatt tacaatcccc taatggaaat    8040
tttcactaat gagatatcat aatgaatgtg aattttattt ctgaaatctc taataaatca    8100
gtcttctccc tggttttccc agctcagcgc ccattacgtt tctgttctct ttcccttagt    8160
ggcattattt gtatcactgt gcatcaggaa agctggctac ggcagcatca atcgggcaga    8220
cacagggtgg ccacggccac tagcggcaag gcggctgccc caagagcgcg gtggcatggc    8280
caccaaagcc actcaatcga gaaagaccgc ggctctgtct acagctcgcg gtgccacggc    8340
cttcttggca gaataaaaat gtagacaagt aataacagag gataatgaaa gaacatactc    8400
tttaaaatat ttcctatttt tttcacagac ccacggtcat taaaaaatgc aattatttac    8460 ttttttttcat ttaaacacat ttcttttgaga ttgagcttttt gggaataacc acctttccac    8520
cattacaata agagataatt tcacgtttag tctaatgtac aaattggatt tttaaaaaat    8580
gagctctatc tgtgaagccc ttattcctat agaatgtgtc ttttttgagtt tattacttat    8640 tacagactct aaaaacaaca ttgctgctga ttttcaagta agctgcctct tctacatagc    8700
```

```
aaataggtac acttcacttt tccctgattt ttcttagggc gtgctattga ttttattgt      8760
tgtctgacaa ataatttat caaacaaaag ggagaaagac taaaaaatgt attttccac       8820
ttttctgtat catgcataat cagcaacaac caatacaata tttggcaaga gtgaacaaaa    8880
ataaatttac ttttgctcct tagaaataca agggttcctt tttagttaca cttttttttt    8940
ttactttgtg tcattcagtt tagagcaatt taatcttttt ttctccaaat ccatttttga    9000
agctgagttt aacttttgca acccatggca aatcttaaat gccctcattt accaatcttt    9060
accaaactcc tatttaagcc tctaaaagtc aatactggcc atcagaccca aatttcagaa    9120
gacaatagtg aaaaattact tacgtttaat ctccagtcgt gtcccttggc cgaagggatc    9180
cacagtgtta acttaattac tttcccctta acaaaaatct cttttcgctg ttaatatcac    9240
taacctgacc gatgcagaga aaatcttgca attgagatgc ctcacttaac tggctagcgc    9300
ttggctgttc cttaagatga actaattttc tatcccttac tcatctgact ttttgaaaga    9360
atctggtact ctttggaatt gacctgagct aatatctcaa acacaaaaac gctccaaatt    9420
taaaaccta taagaaaaag cattaggaaa gtgcacttac gtttgatctc caccttggtc     9480
cctccgccga aagtgagcca cagtgaggga tctcacccct tccctcaac aaaaacctct    9540
cttgaagcca atcatttgag ataggctgct tgttcagaga aaaatctagc tatttcttcc    9600
ccatttcccc catgaatcct attctcctct caaacccaat gattcgtcta tttgctcagc    9660
tttttaagtt cattttctgg tgtcctgcta tttacttctg ggtcaccagg tttattcaac    9720
caaaatatca caaacttgc acaaatgata caatggcact aaaatctcac gaataattga     9780
gacagatgta cttacgtttg atatccactt tggtcccagg gccgaaagtg aatcacagtg    9840
attcgtctta acttttcccct ttacaaaaac ctccctgaaa gctcagcaag cctcttttccc   9900
ccaatgaagt tattttgatt tagaaatctt aaaaattagc cacaagctag cgtcctgtgg    9960
aacaatttcc cctcctctgt acctaacctg ggaatgaagt tgttagatc cctggcatcc    10020
gactaatgaa aatccacaca aaggaacaca aagtaaacta attagcaaca gtgaagaatc    10080
agtggaaaaa agtacttacg tttgatctcc agcttggtcc cctggccaaa agtgtacggg    10140
taaatattat actgttggca gtaataagtt gcaaatctt caggctgcag gctgctgatg    10200
gtgagagtga atctgtccc agatccactg ccgctgaacc ttgatgggac cccactttgc     10260
aaactggatg cagcatagat cagggactta gggctttct ctggtttctg ctgataccag     10320
gctaaccagc tgctaatacc ctgactcgcc cgacaagtga tggtgactct gtctcctaca    10380
gatgcagaca gtgaggatgg agactgggtc atctggatgt cacatctggc acctgagatt    10440
ggaaacataa aaacaaatgt ccacacaatt aatcatgttg taagagaatt ccctgaata     10500
gtaaagcagt actgagcacg ctgggctgag taaactgcta gtgttctcca tccttacctg    10560
ggaaacagag cagcaggagc cccaggagct gagcgaggac cctcatgtcc atgctgtgtc    10620
ctgactgggt ctgattcctg cacaaagtct gaccagccta ttaataaggc ttcagggcag    10680
gaggttgtgc tctgggaaca tgcaaatgag caggggatgg ggcaggctgg gcacagctgc    10740
agagctggcg catctgagta actcagcacc agctcagtgt ccccacctgt cccaggtaag    10800
atcaaggtag ctcaaatttg tctgcagaga atgtgtttct actggggact attttgttat    10860
gggaaacatt ttatggtttc ttttttgacaa tttgaaatat tccttgggag tcgatggagc    10920
aatgtatttc attggtgtat ggggattatt taggagaata ttcttttttg taggaaacac    10980
atagtaaaat tttagaccct acaatttca ggtcttcaaa agactctcat gtgatttctg     11040
ttagggaagg tggtacttat catatacttg caacatttct gtgagtttaa cattgttcct    11100
```

```
ttctaaaaaa aaaattaaaa ataaaattta ttcacatgat gctacatata tttgtaaatg    11160
ttaggtaatg gtgttatgcc attgttctta ccactgtaag atcaagcaat ttacttcaga    11220
tacactaagt tgataccgtg tttcctcaat gcatgcagca attacagatc caccattatc    11280
aagagctcta ggtctcttta atacccagag actaaatggg ctgcaccttc attcctgtttt   11340 gggcaccttc atagtctacc ttcttttctg ccattaagta ttatttccca acattcatct    11400
ctcttagtga gggtgatcat cgcatggagc atgtccctgc cacgcaccat aggtgacact    11460
ttcttctttt acttttatc agggacatca tcctgaccca gacaccaaga tccctgttaa     11520
catcttttgg aaagaggcac tcaatctttt atcaagcaac tgcccatgta catggagaaa    11580
tcaagttggt tccagatgaa actggacagg gatttgcact cgttatatct catatctcta    11640
atgtgcccaa aaatgtcccg gcctggttcc gtgggagggg aagtggatcc aactacatca    11700
gcatcagtgg gctgcagcct aggactccat aaaattttac tgatgcctga ctaggagagc    11760
caaatcacag tgctgtagcc tctgcacaaa ccttcctgct gctttataag ctgcctgaat    11820
tttaagggaa attgcttata ttggaagaaa ggaagaaagc tccatttgtc ctctaaatgt    11880
ttgctgaaaa taaactgaca aaaggaagat taataagaga aaaggcaaac aaaattcact    11940
taaagtgcag caggatatca tagcaaggtg attacccaga taactcaatg ggatccaggt    12000
gtttatgttt cctttctagg gaagaggtaa ttgggaaatg taggcaacct ggagagaata    12060
gatgcgaata gaaatgcatc ctcaaaagaa caggtaatca cctccctagg taaagtatca    12120
actttgagtc tcttccattt ttgattcctc ttttgtgtta atcttccctg acataaaaat    12180
tctcaggaag agttttctta aaaattggtt tccttctgaa gaatttgctt ttaggcaggt    12240
aggggatgtt taggaaaagc cccctgtgca tttcctgctt tctaaatgcc tttggtttta    12300
tataatcatc atacaaatgc agcacagttt gagatgttat tttctggatt cctttacttg    12360
caacccacct gccaagatcc tgttccagag agatgtggct acagactgaa agagcagttt    12420
tcccctcaac aacgtggagg ttggggcact gaccactggt gcagatgaaa acctgtgtag    12480
aacttttgca tctccaactt atgtagtaat agattacttt tgactggaag ccttaatgat    12540
aaaataaata gttgattaac cctttttat gttatacata ttatatactc tattcttcca    12600
ataaagtatg ctaaagaaaa aatgttattg agaaaacctt aaaaatgaga aaatatattt    12660
agtacttatt aagcgcttgc tcacaggtga cacacagaag aaaatataag tggatctgca    12720
aatttcaaac ccaagttatt caagggttaa ctgtaccatg atgaatgtag cagtccccat    12780
ctatagtcta gggcttttcc ctttgctgta tctctgctca tttccaatgg ctatatatat    12840
gtcttatgtg cttcatgatc ttgggcagag aggtctgctt gcatgccttg ctggccagat    12900
ggcctgcaat gtgtatctct taggaaagtg ctatggtttg actgtgtcct ccagaatcca    12960
tcgttataaa gttaaatctc agtgaaatgg tattgccagg tggggcctat tgagatgtgt    13020
tagatcatga gggtggagcc ctctagtgga ataccttaat gccactataa acagggttta    13080
tggggctgga atctctctgt ctcttctgct ggtctgtcat gttaagacat ggccttcgtt    13140
cctttgaagg actgaaagct ccaggcgtca tcttgaaagc agagaaagag gagcttaacc    13200
tgcccatgcc ttgatcttaa atttcccatt ctccagaaat gtgagaaaat aaatttctgt    13260 tcttatgaa ttacacagtg tcaaggaacc taacctgtta tagcagcttg aaagagaaca    13320
agagagacag ctcacaatca gtgaggacag gatgaggtgt atacataccct cagcttcctc   13380 gtctctcagg tggaatagcc cagaggaatt taagtccatg tttccacatg tggttgatct    13440
tcagttatcc tgagtcaggt gggttgttga tgtgtctttt accattcatc ttctgttccc    13500
```

```
tccctcactt tcttcctttc ctcccagtgt aaatttgctg cctaaacagg aatcctcatt    13560
gctggtggac ccaaactaag atagtaaata aaatcattaa tcttttgtat gagggtatt     13620
tctcatctga attcagatcg atgtggtacc tggatcctcg acctgcaggc atgcaagctt    13680
aggaagaaaa atctaaaaaa atgaaagtca cagaaatagc aagtagaatg ctggttacca    13740
gagactgcat tgntaaaggg tacaaaatat cagtctgata gggggactaa gttttggtga    13800
tctgttgcat agcatggcga cattattata tagatgtatt tctggcaggc ttgattgcct    13860
attacatggt aagtcaacat acactaagac actgggggct gctgcagaga aagagattta    13920
atcccaaggc aattaaatga aagacagga ggaagcctca tatctacctc cccaagcact     13980
ttggggttaa agactttaag tggttttgga tggagaggca gattggttga agagtgaagg    14040
atgaagtcat gggactggga ggtgaagaaa ctgctttctt atgttgactc ggttcttgg     14100
gaggggggtg gtctttagac aagttggtgt cagctattct actggaattc aggatctggt    14160
aaatatctca aagattaggt tttatgctca taatggtgaa ggtgttatat ttgggaacaa    14220
tggggacgtt aatggtctgt attttattgca acttgactttt tattagtgag aagctaaggg   14280
aagtggctca gaatgttgtc tgattaatgc ttaactatat ttcagtctgg aacctggaat    14340
actgttcttg ttaaccttat gacagtggtt ttgtagttaa taatactata ttctgtattt    14400
caaaataaca aagtatattc aatgttctca gtacaaaaaa tgataaatat tggaggtgag    14460
gactatgtta attaacctga tttgattatt cgacaatgta tacatgtatg catctcattg    14520
taccccatat gtatatacat tactatttgt caattaaaat caaaataaaa cttttaaaaa    14580
ttcatgtagc cattgcctgg aataaataaa gaaaaatatg tgtgcacatg cttaactata    14640
cccctgtaaa aattgaagct actaagtcca gtaaaatact gaatcacaca tatttctgtc    14700
tttagcttta gtggaaatag tcaaaatact gggtcccaac aatacttata ttagtctttt    14760
cttcccatat ccaccacctt gttatttttt aattcatttg taatacattt agtttcattt    14820
actcttgttt gtaacccatt tggatccgtt gacctgcagg tcgaccggat ccagacatga    14880
taagatacat tgatgagttt ggacaaacca caactagaat gcagtgaaaa aaatgcttta    14940
tttgtgaaat ttgtgatgct attgcttttat ttgtaaccat tataagctgc aataaacaag    15000
ttaacaacaa caattgcatt cattttatgt ttcaggttca gggggaggtg tgggaggttt    15060
tttaaagcaa gtaaaacctc tacaaatgtg gtatggctga ttatgatctc tagtcaaggc    15120
actatacatc aaatattcct tattaaccc  tttacaaatt aaaaagctaa aggtacacaa    15180
tttttgagca tagttattaa tagcagacac tctatgcctg tgtggagtaa gaaaaaacag    15240
tatgttatga ttataactgt tatgcctact tataaaggtt acagaatatt tttccataat    15300
tttcttgtat agcagtgcag cttttttcctt tgtggtgtaa atagcaaagc aagcaagagt    15360
tctattacta aacacagcat gactcaaaaa acttagcaat tctgaaggaa agtccttggg    15420
gtcttctacc tttctcttct tttttggagg agtagaatgt tgagagtcag cagtagcctc    15480
atcatcacta gatggcattt cttctgagca aaacaggttt tcctcattaa aggcattcca    15540
ccactgctcc cattcatcag ttccataggt tggaatctaa aatacacaaa caattagaat    15600
cagtagttta acacattata cacttaaaaa ttttatattt accttagagc tttaaatctc    15660
tgtaggtagt ttgtccaatt atgtcacacc acagaagtaa ggttccttca caaagatccg    15720
gggcccactc ataaatccag ttgccgccac ggtagccaat caccgtatcg tataaatcat    15780
cgtcggtacg ttcggcatcg ctcatcacaa tacgtgcctg gacgtcgagg atttcgcgtg    15840
ggtcaatgcc gcgccagatc cacatcagac ggttaatcat gcgataccag tgagggatgg    15900
```

```
ttttaccatc aagggccgac tgcacaggcg gttgtgcgcc gtgattaaag cggcggacta   15960
gcgtcgaggt ttcaggatgt ttaaagcggg gtttgaacag ggtttcgctc aggtttgcct   16020
gtgtcatgga tgcagcctcc agaatactta ctggaaacta ttgtaacccg cctgaagtta   16080 aaagaacaa cgcccggcag tgccaggcgt tgaaaagatt agcgaccgga gattggcggg    16140
acgaatacga cgcccatatc ccacggctgt tcaatccagg tatcttgcgg gatatcaaca   16200
acatagtcat caaccagcgg acgaccagcc ggttttgcga agatggtgac aaagtgcgct   16260
tttggataca tttcacgaat cgcaaccgca gtaccaccgg tatccaccag gtcatcaata   16320
acgatgaagc cttcgccatc gccttctgcg cgtttcagca ctttaagctc gcgctggttg   16380
tcgtgatcgt agctggaaat acaaacggta tcgacatgac gaatacccag ttcacgcgcc   16440
agtaacgcac ccggtaccag accgccacgg cttacggcaa taatgccttt ccattgttca   16500
gaaggcatca gtcggcttgc gagtttacgt gcatggatct gcaacatgtc ccaggtgacg   16560
atgtattttt cgctcatgtg aagtgtccca gcctgtttat ctacggctta aaaagtgttc   16620
gaggggaaaa taggttgcgc gagattatag agatctggcg cactaaaaac cagtatttca   16680
catgagtccg cgtctttta cgcactgcct ctccctgacg cgggataaag tggtattctc    16740
aaacatatct cgcaagcctg tcttgtgtcc aagctagctt tttgcaaaag cctaggcctc    16800
caaaaaagcc tcctcactac ttctggaata gctcagaggc cgaggcggcc tcggcctctg   16860
cataaataaa aaaattagt cagccatggg gcggagaatg ggcggaactg ggcggagtta    16920
ggggcgggat gggcggagtt aggggcggga ctatggttgc tgactaattg agatgcatgc   16980
tttgcatact tctgcctgct ggggagcctg gttgctgact aattgagatg catgctttgc   17040
atacttctgc ctgctgggga gcctggggac tttccacacc ctaactgaca cacattccac   17100
agctgcctcg cgcgtttcgg tgatgacggt gaaaacctct gacacatgca gctcccggag   17160
acggtcacag cttgtctgta agcggatgcc gggagcagac aagcccgtca gggcgcgtca   17220
gcgggtgttg gcgggtgtcg gggcgcagcc atgacccagt cacgtagcga tagcggagtg   17280
tatactggct taactatgcg gcatcagagc agattgtact gagagtgcac catatgcggt   17340
gtgaaatacc gcacagatgc gtaaggagaa ataccgcat caggcgctct tccgcttcct    17400
cgctcactga ctcgctgcgc tcggtcgttc ggctgcggcg agcggtatca gctcactcaa   17460
aggcggtaat acgttatcc acagaatcag gggataacgc aggaaagaac atgtgagcaa    17520
aaggccagca aaaggccagg aaccgtaaaa aggccgcgtt gctggcgttt ttccataggc   17580
tccgcccccc tgacgagcat cacaaaaatc gacgctcaag tcagaggtgg cgaaacccga   17640
caggactata agataccag gcgtttcccc ctggaagctc cctcgtgcgc tctcctgttc     17700
cgaccctgcc gcttaccgga tacctgtccg ccttctccc ttcgggaagc gtggcgcttt     17760
ctcatagctc acgctgtagg tatctcagtt cggtgtaggt cgttcgctcc aagctgggct   17820
gtgtgcacga accccccgtt cagcccgacc gctgcgcctt atccggtaac tatcgtcttg   17880
agtccaaccc ggtaagacac gacttatcgc cactggcagc agccactggt aacaggatta   17940
gcagagcgag gtatgtaggc ggtgctacag agttcttgaa gtggtggcct aactacggct   18000
acactagaag gacagtattt ggtatctgcg ctctgctgaa gccagttacc ttcggaaaaa   18060
gagttggtag ctcttgatcc ggcaaacaaa ccaccgctgg tagcggtggt ttttttgttt   18120
gcaagcagca gattacgcgc agaaaaaaag gatctcaaga agatcctttg atcttttcta   18180
cggggtctga cgctcagtgg aacgaaaact cacgttaagg gattttggtc atgagattat   18240
caaaaaggat cttcacctag atccttttaa attaaaaatg aagttttaaa tcaatctaaa   18300
```

```
gtatatatga gtaaacttgg tctgacagtt accaatgctt aatcagtgag gcacctatct    18360
cagcgatctg tctatttcgt tcatccatag ttgcctgact ccccgtcgtg tagataacta    18420
cgatacggga gggcttacca tctggcccca gtgctgcaat gataccgcga gacccacgct    18480
caccggctcc agattatca gcaataaacc agccagccgg aagggccgag cgcagaagtg    18540
gtcctgcaac tttatccgcc tccatccagt ctattaattg ttgccgggaa gctagagtaa    18600
gtagttcgcc agttaatagt ttgcgcaacg ttgttgccat tgctgcaggc atcgtggtgt    18660
cacgctcgtc gtttggtatg gcttcattca gctccggttc ccaacgatca aggcgagtta    18720
catgatcccc catgttgtgc aaaaaagcgg ttagctcctt cggtcctccg atcgttgtca    18780
gaagtaagtt ggccgcagtg ttatcactca tggttatggc agcactgcat aattctctta    18840
ctgtcatgcc atccgtaaga tgcttttctg tgactggtga gtactcaacc aagtcattct    18900
gagaatagtg tatgcggcga ccgagttgct cttgcccggc gtcaacacgg gataataccg    18960
cgccacatag cagaacttta aaagtgctca tcattggaaa acgttcttcg ggcgaaaac    19020 tctcaaggat cttaccgctg ttgagatcca gttcgatgta acccactcgt gcacccaact    19080
gatcttcagc atctttttact ttcaccagcg tttctgggtg agcaaaaaca ggaaggcaaa    19140
atgccgcaaa aaagggaata agggcgacac ggaaatgttg aatactcata ctcttccttt    19200
ttcaatatta ttgaagcatt tatcagggtt attgtctcat gagcggatac atatttgaat    19260
gtatttagaa aaataaacaa ataggggttc cgcgcacatt tccccgaaaa gtgccacctg    19320
acgtctaaga aaccattatt atcatgacat taacctataa aaataggcgt atcacgaggc    19380
cctttcgtct tcaagaagaa ttccaagcta tt                                 19412
```

<210> SEQ ID NO 13
<211> LENGTH: 11
<212> TYPE: DNA
<213> ORGANISM: Mus musculus

<400> SEQUENCE: 13
agtgactgac g                                                               11

<210> SEQ ID NO 14
<211> LENGTH: 9
<212> TYPE: DNA
<213> ORGANISM: Mus musculus

<400> SEQUENCE: 14 ttccctgaa                                                                   9

<210> SEQ ID NO 15
<211> LENGTH: 15
<212> TYPE: DNA
<213> ORGANISM: Mus musculus

<400> SEQUENCE: 15
gcaggaagtg aaagt                                                           15

<210> SEQ ID NO 16
<211> LENGTH: 7
<212> TYPE: DNA
<213> ORGANISM: Mus musculus

<400> SEQUENCE: 16 ggaaagt                                                                     7

<210> SEQ ID NO 17

-continued

```
<211> LENGTH: 9
<212> TYPE: DNA
<213> ORGANISM: Mus musculus

<400> SEQUENCE: 17 tttgggagg                                                                 9

<210> SEQ ID NO 18
<211> LENGTH: 9
<212> TYPE: DNA
<213> ORGANISM: Mus musculus

<400> SEQUENCE: 18 caaaatggc                                                                 9

<210> SEQ ID NO 19
<211> LENGTH: 13
<212> TYPE: DNA
<213> ORGANISM: Mus musculus

<400> SEQUENCE: 19
agttagccaa tgg                                                           13

<210> SEQ ID NO 20
<211> LENGTH: 8
<212> TYPE: DNA
<213> ORGANISM: Mus musculus

<400> SEQUENCE: 20 tgacgtag                                                                  8

<210> SEQ ID NO 21
<211> LENGTH: 15
<212> TYPE: DNA
<213> ORGANISM: Mus musculus

<400> SEQUENCE: 21
aaaaatgaaa gaact                                                         15

<210> SEQ ID NO 22
<211> LENGTH: 15
<212> TYPE: DNA
<213> ORGANISM: Mus musculus

<400> SEQUENCE: 22
ggaagtgaaa gtaat                                                         15

<210> SEQ ID NO 23
<211> LENGTH: 12
<212> TYPE: DNA
<213> ORGANISM: Mus musculus

<400> SEQUENCE: 23
gtgctaatga aa                                                            12

<210> SEQ ID NO 24
<211> LENGTH: 10
<212> TYPE: DNA
<213> ORGANISM: Mus musculus

<400> SEQUENCE: 24
tttcattttt                                                               10

<210> SEQ ID NO 25
```

-continued

```
<211> LENGTH: 6
<212> TYPE: DNA
<213> ORGANISM: Mus musculus

<400> SEQUENCE: 25 tcagca                                                                   6

<210> SEQ ID NO 26
<211> LENGTH: 6
<212> TYPE: DNA
<213> ORGANISM: Mus musculus

<400> SEQUENCE: 26 catgtg                                                                   6

<210> SEQ ID NO 27
<211> LENGTH: 9
<212> TYPE: DNA
<213> ORGANISM: Mus musculus

<400> SEQUENCE: 27 tgatgtaat                                                                9

<210> SEQ ID NO 28
<211> LENGTH: 12
<212> TYPE: DNA
<213> ORGANISM: Mus musculus

<400> SEQUENCE: 28
ggtgcagcaa tg                                                           12

<210> SEQ ID NO 29
<211> LENGTH: 6
<212> TYPE: DNA
<213> ORGANISM: Mus musculus

<400> SEQUENCE: 29 cttctc                                                                   6

<210> SEQ ID NO 30
<211> LENGTH: 8
<212> TYPE: DNA
<213> ORGANISM: Mus musculus

<400> SEQUENCE: 30 atttgcat                                                                 8

<210> SEQ ID NO 31
<211> LENGTH: 6
<212> TYPE: DNA
<213> ORGANISM: Mus musculus

<400> SEQUENCE: 31 ttcaaa                                                                   6

<210> SEQ ID NO 32
<211> LENGTH: 10
<212> TYPE: DNA
<213> ORGANISM: Mus musculus

<400> SEQUENCE: 32
tggcctttcc                                                              10

<210> SEQ ID NO 33
```

```
<211> LENGTH: 8
<212> TYPE: DNA
<213> ORGANISM: Mus musculus

<400> SEQUENCE: 33 atttgcat                                                                   8

<210> SEQ ID NO 34
<211> LENGTH: 10
<212> TYPE: DNA
<213> ORGANISM: Mus musculus

<400> SEQUENCE: 34
tatgcaaatg                                                                10

<210> SEQ ID NO 35
<211> LENGTH: 15
<212> TYPE: DNA
<213> ORGANISM: Mus musculus

<400> SEQUENCE: 35
ccgaatatgc aattc                                                          15

<210> SEQ ID NO 36
<211> LENGTH: 7
<212> TYPE: DNA
<213> ORGANISM: Mus musculus

<400> SEQUENCE: 36 aatttcc                                                                    7

<210> SEQ ID NO 37
<211> LENGTH: 12
<212> TYPE: DNA
<213> ORGANISM: Mus musculus

<400> SEQUENCE: 37
gcttttccta aa                                                             12

<210> SEQ ID NO 38
<211> LENGTH: 8
<212> TYPE: DNA
<213> ORGANISM: Mus musculus

<400> SEQUENCE: 38 cttcccct                                                                   8

<210> SEQ ID NO 39
<211> LENGTH: 12
<212> TYPE: DNA
<213> ORGANISM: Mus musculus

<400> SEQUENCE: 39
cattgctcca tc                                                             12

<210> SEQ ID NO 40
<211> LENGTH: 15
<212> TYPE: DNA
<213> ORGANISM: Mus musculus

<400> SEQUENCE: 40
ctcatttgca tgttc                                                          15

<210> SEQ ID NO 41
```

-continued

```
<211> LENGTH: 10
<212> TYPE: DNA
<213> ORGANISM: Mus musculus

<400> SEQUENCE: 41
ggaacaatgt                                                          10

<210> SEQ ID NO 42
<211> LENGTH: 7
<212> TYPE: DNA
<213> ORGANISM: Mus musculus

<400> SEQUENCE: 42 ttaagtg                                                              7

<210> SEQ ID NO 43
<211> LENGTH: 10
<212> TYPE: DNA
<213> ORGANISM: Mus musculus

<400> SEQUENCE: 43
gggcttttcc                                                          10

<210> SEQ ID NO 44
<211> LENGTH: 11
<212> TYPE: DNA
<213> ORGANISM: Mus musculus

<400> SEQUENCE: 44
gacaggtggg g                                                        11

<210> SEQ ID NO 45
<211> LENGTH: 11
<212> TYPE: DNA
<213> ORGANISM: Mus musculus

<400> SEQUENCE: 45
ggcaggtggg t                                                        11

<210> SEQ ID NO 46
<211> LENGTH: 9
<212> TYPE: DNA
<213> ORGANISM: Mus musculus

<400> SEQUENCE: 46 ttcccataa                                                            9

<210> SEQ ID NO 47
<211> LENGTH: 12
<212> TYPE: DNA
<213> ORGANISM: Mus musculus

<400> SEQUENCE: 47
tatcattaag gc                                                       12

<210> SEQ ID NO 48
<211> LENGTH: 13
<212> TYPE: DNA
<213> ORGANISM: Mus musculus

<400> SEQUENCE: 48
catacaccaa tga                                                      13

<210> SEQ ID NO 49
```

```
<211> LENGTH: 6
<212> TYPE: DNA
<213> ORGANISM: Mus musculus

<400> SEQUENCE: 49 catgtg                                                                    6

<210> SEQ ID NO 50
<211> LENGTH: 6
<212> TYPE: DNA
<213> ORGANISM: Mus musculus

<400> SEQUENCE: 50 catgtg                                                                    6

<210> SEQ ID NO 51
<211> LENGTH: 7
<212> TYPE: DNA
<213> ORGANISM: Mus musculus

<400> SEQUENCE: 51 aggtaat                                                                   7

<210> SEQ ID NO 52
<211> LENGTH: 14
<212> TYPE: DNA
<213> ORGANISM: Mus musculus

<400> SEQUENCE: 52
aaatgttgca agta                                                          14

<210> SEQ ID NO 53
<211> LENGTH: 6
<212> TYPE: DNA
<213> ORGANISM: Mus musculus

<400> SEQUENCE: 53 acatgg                                                                    6

<210> SEQ ID NO 54
<211> LENGTH: 7
<212> TYPE: DNA
<213> ORGANISM: Mus musculus

<400> SEQUENCE: 54 caggaag                                                                   7

<210> SEQ ID NO 55
<211> LENGTH: 6
<212> TYPE: DNA
<213> ORGANISM: Mus musculus

<400> SEQUENCE: 55 ttcaaa                                                                    6

<210> SEQ ID NO 56
<211> LENGTH: 8
<212> TYPE: DNA
<213> ORGANISM: Mus musculus

<400> SEQUENCE: 56 atttgcat                                                                  8
```

ANTI-IL-12 ANTIBODY BASED VECTORS, HOST CELLS, AND METHODS OF PRODUCTION AND USES

CROSS REFERENCE TO RELATED APPLICATIONS

This application is a divisional of U.S. application Ser. No. 11/722,281, filed 20 Jun. 2007, now U.S. Pat. No. 7,736,650, issued 15 Jun. 2010, which is a national stage of International Application Number PCT/US2005/046885, filed 21 Dec. 2005, which claims the benefit of U.S. Provisional Application No. 60/637,936, filed 21 Dec. 2004. The entire contents of each of the aforesaid applications are incorporated herein by reference in their entireties.

FIELD OF THE INVENTION

The present invention relates to vectors and plasmids directing expression of an antibody, host cells, and methods of making and using thereof, including specific vector enhancer and promoter sequences and their interaction with host cell transcription factors.

BACKGROUND

Antibody molecules consist of a combination of two heavy (H) chain and two light (L) chain polypeptides. Each heavy and light chain comprises a constant region containing the CL, CH1, hinge region, CH2, and CH3 regions, and a variable region containing the hypervariable regions (complement determining regions (CDRs)); the CDRs control the antibody's antigen-binding characteristics. The two heavy chains are joined to each other and the light chains in a Y-shaped structure via disulfide bridges such that the variable regions of the light chains ($V_L$) and heavy chains ($V_H$) are located next to each other.

To generate antibodies, conventional hybridoma techniques have been used in which clones of hybrid cells expressing genes coding for the light and heavy chains of an antibody molecule are obtained by immunization with an antigen molecule. This technique necessitates the fusion of cells of lymphocytic origin, containing the genes for antibody formation and cells forming immortal lines. The cells carrying the genes in question are generally obtained by random creation of libraries of circulating cells, and screening of the hybridomas with an antigen-antibody reaction after the hybridoma clones are multiplied and cultured. This technique can be uncertain and laborious with limited yield of antibodies, and is limited in application to non-human (e.g., mouse) antibody production.

In addition, monoclonal antibodies and their fragments can be expressed in various host systems, such as *E. coli*, yeast, and mammalian host cells. In general, a mammalian expression vector will contain (1) regulatory elements, usually in the form of viral promoter or enhancer sequences and characterized by a broad host and tissue range; (2) a "polylinker" sequence, facilitating the insertion of a DNA fragment within the plasmid vector; and (3) the sequences responsible for intron splicing and polyadenylation of mRNA transcripts. This contiguous region of the promoter-polylinker-polyadenylation site is commonly referred to as the transcription unit. The vector will likely also contain (4) a selectable marker gene(s) (e.g., the .beta.-lactamase gene), often conferring resistance to an antibiotic (such as ampicillin), allowing selection of initial positive transformants in *E. coli*; and (5) sequences facilitating the replication of the vector in both bacterial and mammalian hosts.

Unlike most genes that are transcribed from continuous genomic DNA sequences, antibody genes are assembled from gene segments that may be widely separated in the germ line. In particular, heavy chain genes are formed by recombination of three genomic segments encoding the variable (V), diversity (D) and joining (J)/constant (C) regions of the antibody. Functional light chain genes are formed by joining two gene segments; one encodes the V region and the other encodes the J/C region. Both the heavy chain and .kappa. light chain loci contain many V gene segments (estimates vary between 100 s and 1000 s) estimated to span well over 1000 kb. The .lambda. locus is, by contrast, much smaller and has been shown to span approximately 300 kb on chromosome 16 in the mouse. It consists of four joining/constant region gene segments and two variable gene segments. Recombination resulting in functional genes occurs predominantly between $V_1$ and either $J_1/C_1$ or $J_3/C_3$ elements or between $V_2$ and $J_2/C_2$ elements ($J_4/C_4$ is a pseudogene), although recombinations between $V_2$ and $J_3/C_3$ or $J_1/C_1$ are seen very rarely.

An example of a mammalian expression vector is CDM8. The transcription unit of CDM8 is composed of a chimeric promoter (the human cytomegalovirus AD169 constitutive promoter fused to the T7 RNA polymerase promoter), a polylinker region and the SV40 small tumor (t) antigen splice and early region polyadenylation signals derived from pSV2. The human cytomegalovirus (HCMV) promoter is expressed in a variety of mammalian cell types, while the T7 bacteriophage DNA-dependent RNA polymerase promoter can drive in vitro cell-free transcription/translation of cloned inserts. This particular promoter fusion allows initial experiments to be conducted within the confines of the host mammalian cell type, while further analysis and utilization of the cloned insert may potentially be carried out in an in vitro "cell-free" transcription/translation system. The constitutively expressed HCMV promoter has also been utilized in other mammalian expression vectors besides CDM8. Origins of replication in CDM8 include (1) .pi.VX (allowing e.g., replication in *E. coli*) (2) SV40 origin (e.g., allowing replication in a variety of COS cell types) (3) polyoma origin (e.g., allowing replication in polyoma virus transformed mouse fibroblasts) and (4) the bacteriophage M13 origin (e.g., allowing generation of single-stranded template for DNA sequence analysis and/or oligonucleotide site-directed mutagenesis).

Furthermore, CDM8 carries the supF gene for selection in *E. coli*. In this antibiotic selection system, a CDM8-based plasmid construction is transformed into a specialized *E. coli* strain containing an episome carrying genes encoding resistance to the antibiotics, ampicillin and tetracyline. However, both genes contain chain termination ("nonsense" codon) point mutations inactivating the resistance phenotype. The supF gene product, a nonsense suppressor tRNA, restores the resistant phenotype for each antibiotic. Therefore, selection is based on growth of the specialized episomal-carrying *E. coli* strain on media containing ampicillin and tetracycline. Colonies exhibiting this phenotype are supposedly transformed with the CDM8-based plasmid construction.

The CDM8 vector is compatible with COS cell lines as well as cell lines transformed with the polyoma virus. COS cell lines are African green monkey CV1 cells transformed with an origin-defective SV40 mutant virus. The COS cells produce the large T antigen, which is required in trans to promote replication of SV40 or plasmid constructions, such as CDM8, which contain the respective cis-acting sequences initiating viral replication. Therefore, COS cells transfected with a CDM8-based construction will support replication of the plasmid, resulting in increased plasmid copy number and a transient overexpression of the gene of interest.

The major use of CDM8 is cDNA expression cloning and overproduction of specific proteins in a mammalian in vitro expression system. Expression cloning takes on various forms depending on the mode of detection utilized to identify the cDNA of interest; however, the initial step consists of isolating mRNA and synthesizing double-stranded deoxyribonucleic acid copies of the mRNA population (cDNAs). These cDNAs must be efficiently ligated to a plasmid or bacteriophage DNA cloning vector and transferred to the appropriate host prior to library screening and analysis. The CDM8 vector contains two BstXI restriction sites, making it amenable to the "adaptor" linker procedure of ligating cDNAs to the vector, i.e., the use of DNA fragments blunt ended at one end (and therefore compatible for ligation with the blunt ended cDNA) but containing a non-palindromic overhang (sticky end) on the other end (in this instance, compatible for ligation with BstXI digested vector DNA, but not with other cDNAs).

Another example of a mammalian expression vector is pCMX. This vector contains: (1) the immediate early promoter of HCMV, (2) an SV40 RNA splice/polyadenylation sequence, (3) an SV40 origin of replication, (4) a pBR322 origin of replication, and (5) a selectable marker conferring resistance to an antibiotic, such as the .beta.-lactamase gene conferring resistance to the antibiotic ampicillin. The pCMX vector can also be used for the transient expression of a cloned DNA sequence in transfected COS cells.

Control of transcription of both rearranged heavy and .kappa. light chain genes depends both on the activity of a tissue specific promoter upstream of the V region and a tissue specific enhancer located in the J-C intron. These elements act synergistically. Also, a second B-cell specific enhancer has been identified in the .kappa. light chain locus. This further enhancer is located 9 kb downstream of C.sub..kappa..

One such mammalian host system used to produce antibodies is a mouse myeloma host cell that has been transfected with cloned DNA encoding the desired antibody. Such "recombinant monoclonal antibodies" are often distinct from hybridoma-derived monoclonal antibodies for which the DNA has not been cloned and for which the cells producing the monoclonal antibody are derived by immortalizing a natural monoclonal antibody-producing cell isolated from an animal. The heavy and light chain immunoglobulin (Ig) genes being expressed in hybridoma cells are under the control of the natural endogenous promoter that had always been linked to the particular variable region sequence being expressed as opposed to the promoter contained in the recombinant vector.

In recombinant production, the monoclonal antibody sequence to be cloned must be ligated into an appropriate vector after restriction enzyme treatment of the vector. This task can be difficult and imprecise as the process of incorporating the antibody nucleotide sequence(s) into an expression vector or plasmid is complex.

However, by cloning the monoclonal antibody DNA sequences prior to preparing transfected cell-derived monoclonal antibodies, recombinant DNA methods can be used to replace the natural endogenous promoter for an Ig gene with any promoter of choice. A primary reason for changing a promoter is to realize higher monoclonal antibody production levels.

Promoter sequences, in conjunction with downstream enhancer sequences, are responsible for driving transcription (i.e., RNA synthesis) of the heavy and light chain genes in the transfected cells by binding to specialized nuclear proteins called transcription factors. It has become apparent that there are fewer sites for transcription factor binding in an Ig promoter than there are in an Ig enhancer; however, the fact that there is sequence variability among promoters but only a single copy of an enhancer sequence makes it highly likely that there is functional variability among Ig promoters. One promoter may be "strong," i.e., efficient at binding a favorable combination of transcription factors that leads to high levels of monoclonal antibody RNA synthesis, whereas another promoter may be "weak," due to having a different DNA sequence. Since each of the more than 200 variable region HC genes and the more than 200 variable region LC genes in an Ig repertoire has its own naturally linked promoter, and it is likely that no two promoters have identical sequences, the many different Ig promoters are likely to vary significantly with respect to how well they drive transcription.

Ig promoters are only functional in lymphoid-type host cells, such as T cells and B cells (and myeloma cells), due to their requirement for Ig gene-specific transcription factors (for example, Oct-2 and OBF-1) not expressed in other cell types. In addition, even lymphoid cell-specific transcription factors may be expressed only at particular stages of cellular differentiation such that optimal expression may depend on matching the differentiation state of the host cell line with the appropriate sequence motifs in the Ig gene promoters. Although the host cell specificity of Ig promoters may be seen as a minor disadvantage for expression of the monoclonal antibody in a non-lymphoid host cell, the large assortment of HC and LC promoters affords a chance to identify and perhaps further optimize strong promoters that can be incorporated into lymphoid cell-specific vectors.

Expression of monoclonal antibodies behind a strong promoter increases the chances of identifying high-producing cell lines and obtaining higher yields of monoclonal antibodies. Consequently, Ig vectors with strong promoters are highly desirable for expressing any monoclonal antibody of interest. In addition, vectors with unique DNA cloning sites downstream of strong promoters would have an added convenience.

Accordingly, there is a need for new vectors and plasmids useful for expression of antibodies that simplify ligation techniques and enable customization of enhancer and promoter sequences in order to increase antibody production.

SUMMARY OF THE INVENTION

The present invention relates to recombinant expression vectors and plasmids comprising restriction sites for cloning of various antibodies. In another embodiment, the invention provides expression control sequences in the vector, such as enhancer and promoter sequences, that can be customized related to the antibody gene to be cloned and transcribed and the host cell type to be used, in order to drive transcription efficiently. The present invention also comprises isolated host cells, e.g., mammalian and non-mammalian cells, containing such a vector or plasmid. The invention further provides methods for producing an antibody by culturing, in a suitable medium, a host cell containing a recombinant expression vector of the invention such that the antibody is produced.

In another embodiment, the invention comprises a method for identifying, modulating, and/or determining the interaction between host cell transcription factors and promoter and enhancer sequences of an expression vector. This interaction drives the transcription process. The transcription factors and promoter and enhancer sequences can be customized to improve their affinity for or binding to each other, which can increase the yield and efficiency of the transcription process.

The present invention further provides any invention described herein.

DESCRIPTION OF THE INVENTION

Figure 1A:
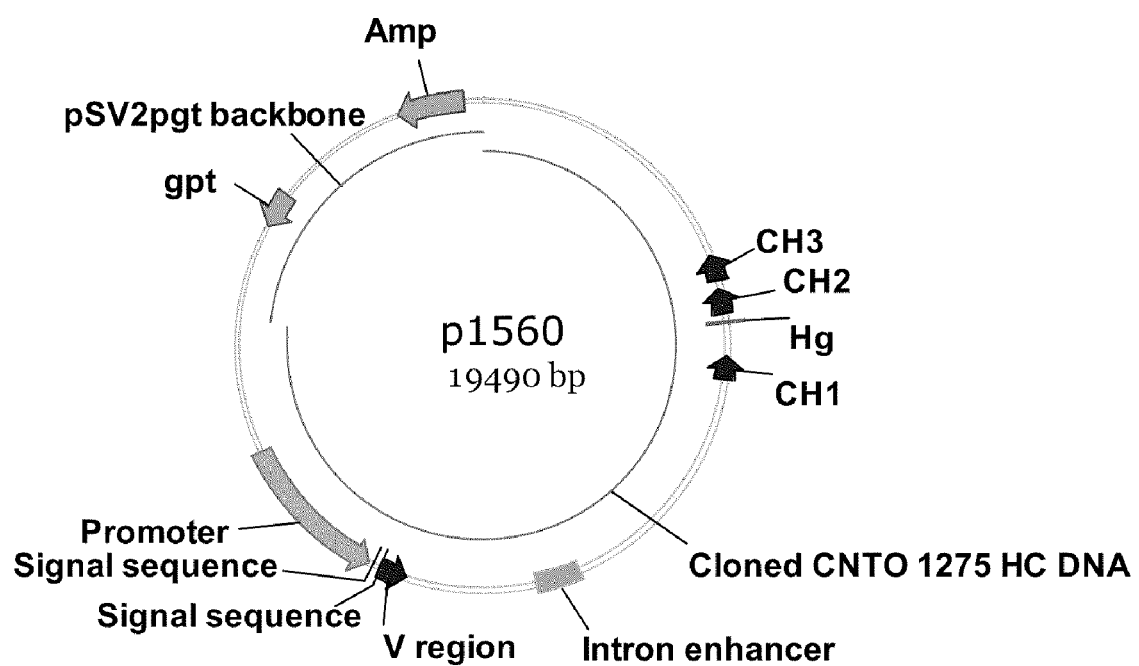
FIG. 1A is a schematic depiction of the vector map for plasmid p1560.

The following definitions are set forth to illustrate and define the meaning and scope of various terms used to describe the invention herein.

An "activity," a biological activity, and a functional activity of a polypeptide refer to an activity exerted by a protein or polypeptide in response to its specific interaction with another protein or molecule as determined in vivo, in situ, or in vitro, according to standard techniques. Such activities can be a direct activity, such as an association with or an enzymatic activity on a second protein, or an indirect activity, such as a cellular process mediated by interaction of the protein with a second protein or a series of interactions as in intracellular signalling or the coagulation cascade.

An "antibody" includes any polypeptide or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion, fragment or variant thereof. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. For example, antibody fragments include, but are not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, et al., eds., Current Protocols in Immunology, John Wiley & Sons, Inc., NY (1994-2001); Colligan et al., Current Protocols in Polypeptide Science, John Wiley & Sons, NY, N.Y., (1997-2001)).

"Chimeric" or "fusion" molecules are nucleic acids or polypeptides that are created by combining one or more of polynucleotides (or their parts) with additional nucleic acid sequence(s). Such combined sequences may be introduced into an appropriate vector and expressed to give rise to a chimeric or fusion polypeptide.

"Complement of" or "complementary to" a nucleic acid sequence of the invention refers to a polynucleotide molecule having a complementary base sequence and reverse orientation as compared to a first polynucleotide.

"Fragment" is a variant polypeptide having an amino acid sequence that is entirely the same as part but not all of any amino acid sequence of a polypeptide or a variant polynucleotide having a nucleic acid sequence that is entirely the same as part but not all of any nucleic acid sequence of any polynucleotide. Fragments can include, e.g., truncation polypeptides having a portion of an amino acid sequence, or of variants thereof, such as a continuous series of residues that includes a heterologous amino- and/or carboxy-terminal amino acid sequence. Degradation forms of the polypeptides produced by or in a host cell are also included. Other exemplary fragments are characterized by structural or functional attributes, such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions, and high antigenic index regions.

Further exemplary fragments include an isolated polypeptide comprising an amino acid sequence having at least 15, 20, 30, 40, 50 or 100 contiguous amino acids from a full-length amino acid sequence, or an isolated polypeptide comprising an amino acid sequence having at least 15, 20, 30, 40, 50 or 100 contiguous amino acids truncated or deleted from the full-length amino acid sequence. Fragments also include isolated polynucleotides having similar sizes and characteristics.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990). The BLAST X program is publicly available from NCBI and other sources (BLAST Manual, Altschul, S., et al., NCBINLM NIH Bethesda, Md. 20894: Altschul, S., et al., J. Mol. Biol. 215: 403-410 (1990). The well-known Smith Waterman algorithm may also be used to determine identity.

Preferred parameters for polypeptide sequence comparison include the following:
(1) Algorithm: Needleman and Wunsch, J. Mol. Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:
(1) Algorithm: Needleman and Wunsch, J. Mol. Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to a sequence, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

$n_n \le x_n - (x_n \cdot y)$, wherein $n_n$ is the number of nucleotide alterations, $x_n$ is the total number of nucleotides in the sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding a polypeptide may create nonsense, missense or frameshift mutations in this coding sequence and thereby alter the polypeptide encoded by the polynucleotide following such alterations. Similarly, a polypeptide sequence may be identical to a reference sequence, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the sequence by the numerical percent of the respective percent identity (divided by 100) and then subtracting that product from the total number of amino acids in the sequence, or:

$n_a \le x_a - (x_a \cdot y)$, wherein $n_a$ is the number of amino acid alterations, $x_a$ is the total number of amino acids in the sequence, and y is, for instance 0.70 for 70%, 0.80 for 80%, 0.85 for 85% etc., and wherein any non-integer produce of $x_a$ and y is rounded down to the nearest integer prior to subtracting it from $x_a$.

"Nucleic acids" are polymers of nucleotides, wherein a nucleotide comprises a base linked to a sugar which sugars are in turn linked one to another by an interceding at least bivalent molecule, such as phosphoric acid. In naturally occurring nucleic acids, the sugar is either 2'-deoxyribose (DNA) or ribose (RNA). Unnatural poly- or oliogonucleotides contain modified bases, sugars, or linking molecules, but are generally understood to mimic the complementary nature of the naturally occurring nucleic acids after which they are designed. An example of an unnatural oligonucleotide is an antisense molecule composition that has a phosphorothioate backbone. An "oligonucleotide" generally refers to nucleic acids having less than 30 nucleotides.

A "polypeptide" is a polymer of amino acid residues joined by peptide bonds, and a peptide generally refers to amino acid polymers of 12 or less residues. Peptide bonds can be produced naturally as directed by the nucleic acid template or synthetically by methods well known in the art.

A "protein" is a macromolecule comprising one or more polypeptide chains. A protein may further comprise substituent groups attached to the side groups of the amino acids not involved in formation of the peptide bonds. Typically, proteins formed by eukaryotic cell expression also contain carbohydrates. Proteins are defined herein in terms of their amino acid sequence or backbone and substituents are not specified, whether known or not.

The term "receptor" denotes a molecule having biological activity resulting from interaction with a specific ligand or binding partner. Cell membrane bound receptors are characterized by an extracellular ligand-binding domain, one or more membrane spanning or transmembrane domains, and an intracellular effector domain that is typically involved in signal transduction. Ligand binding to cell membrane receptors causes changes in the extracellular domain that are communicated across the cell membrane, direct or indirect interaction with one or more intracellular proteins, and alters cellular properties, such as enzyme activity, cell shape, or gene expression profile. Receptors may also be untethered to the cell surface and may be cytosolic, nuclear, or released from the cell altogether. Non-cell associated receptors are termed soluble receptors.

All publications or patents cited herein are entirely incorporated herein by reference, whether or not specifically designated accordingly, as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley &

Sons, Inc., NY (1994-2001); Colligan et al., Current Protocols in Protein Science, John Wiley & Sons, NY, N.Y., (1997-2001).

Recombinant Expression Vectors and Host Cells

The invention provides vectors, preferably, expression vectors, containing a nucleic acid encoding a specific polypeptide, for example, the anti-IL-12 antibody, or may be used to obtain plasmids containing various antibody HC or LC genes or portions thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, e.g., expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). In addition, the regulatory sequence is optimized based on the host cell characterisitics, i.e., transcription factors.

The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion and chimeric proteins or peptides, encoded by nucleic acids as described herein.

The recombinant expression vectors of the invention can be designed for expression of a polypeptide in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione 5-transferase (GST), maltose E binding protein, or protein A, respectively, to the target recombinant protein.

To assist in affinity purification, various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol, 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering 3(6):547-553 (1990)). Other tag polypeptides include the Flag-peptide (Hopp et al., Bio Technology, 6:1204-1210 (1988)); the KT3 epitope peptide (Martin et al., Science, 255:192-194 (1992)); an .alpha.-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)). A preferred tag is the FLAG tag.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in host bacteria with an impaired capacity to proteolytically cleave the recombinant protein (Gottesman, *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al. (1987) *EMBO J.* 6:229-234), pMFa (Kurjan and Herskowitz, (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells, see chapters 16 and 17 of Sambrook et al., supra.

In another embodiment, the recombinant mammalian expression vector is capable of directing expression of the nucleic acid, preferentially in a particular cell type, such as lymphoma cells (e.g., mouse myeloma cells). In specific cell types, tissue-specific regulatory elements are used to express the nucleic acid. Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular, promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, by the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule cloned into the expression vector in an antisense orientation. That is, the DNA molecule is operably linked to a regulatory sequence in a manner that allows for expression (by transcription of the DNA molecule) of an RNA molecule that is antisense to the mRNA encoding a polypeptide. Regulatory sequences operably linked to a nucleic acid cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells). A number of suitable mammalian host cell lines capable of expressing intact glycosylated polypeptides have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org).

Expression vectors for these cells can include one or more of the following expression control sequences, a promoter, an enhancer, and/or processing information sites, such as ribosome binding sites, RNA splice sites, polyadenylation sites, and transcriptional terminator sequences (See, e.g., Ausubel et al., supra; Sambrook, et al., supra).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as, chloramphenicol, tetracyclines, gentamycin, kanamycin, ampicillin, G418, hygromycin, methotrexate, etc. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide (e.g., a protein or antibody). Accordingly, the invention further provides methods for producing a polypeptide using the host cells of the invention. In one embodiment, the method comprises culturing the host cell of the invention (into which a recombinant expression vector encoding a polypeptide has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which at least one sequence encoding a polypeptide has been introduced. Such host cells can then be used to create non-human transgenic animals in which exogenous sequences encoding a polypeptide have been introduced into their genome or homologous recombinant animals in which endogenous sequences encoding a polypeptide have been altered. Such animals are useful for studying the function and/or activity of the polypeptide and for identifying and/or evaluating modulators of polypeptide activity. As used herein, a "transgenic animal" is a non-human animal, preferably, a mammal, more preferably, a rodent, such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide to particular cells. Methods for generating transgenic animals via embryo manipulation and microinjection, particularly, animals such as mice, have become conventional in the art and are described, for example, in U.S. Pat. Nos. 4,736,866, 4,870,009, and 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create a homologous recombinant animal, a vector is prepared which contains at least a portion of a gene encoding a polypeptide into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication Nos. WO 97/07668 and WO 97/07669.

Antibodies

The present invention further includes, but is not limited to, methods of using nucleic acids and polypeptides encoded thereby to make antibodies and anti-idiotype antibodies, including diagnostic and therapeutic compositions, methods and devices. Such antibodies optionally further affect a specific ligand, such as but not limited to, where such antibody modulates, decreases, increases, antagonizes, agonizes, mitigates, aleviates, blocks, inhibits, abrogates and/or interferes with at least one protein activity or binding, or with receptor activity or binding, in vitro, in situ and/or in vivo. As a non-limiting example, a suitable antibody, specified portion or variant can bind at least one protein, or specified portions, variants or domains thereof. A suitable antibody, specified portion, or variant can also optionally affect at least one of protein activity or function, such as but not limited to, RNA, DNA or polypeptide synthesis, protein release, receptor signaling, membrane cleavage, protein activity, protein production and/or synthesis. Antibodies useful in the methods and compositions of the present invention can optionally be characterized by high affinity binding to their antigens and, optionally and preferably, having low toxicity.

As used herein, an "antibody," and the like include any polypeptide or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion, fragment or variant thereof, or at least one portion of a receptor or binding polypeptide, which can be incorporated into an antibody.

Antibodies can include one or more of at least one CDR, at least one variable region, at least one constant region, at least one heavy chain (e.g., g1, g2, g3, g4, m, a1, a2, d, e), at least one light chain (e.g., kappa and lambda), or any portion or fragment thereof, and can further comprise interchain and intrachain disulfide bonds, hinge regions, glycosylation sites that can be separated by a hinge region, as well as heavy chains and light chains. Light chains typically have a molecular weight of about 25 Kd and heavy chains typically range from 50K-77 Kd. Light chains can exist in two distinct forms or isotypes, kappa (k) and lambda (l), which can combine with any of the heavy chain types. All light chains have at least one variable region and at least one constant region. The IgG antibody is considered a typical antibody structure and has two intrachain disulfide bonds in the light chain (one in variable region and one in the constant region), with four in the heavy chain, and such bond encompassing a peptide loop of about 60-70 amino acids comprising a "domain" of about 110 amino acids in the chain. IgG antibodies can be characterized into four classes, IgG1, IgG2, IgG3 and IgG4. Each immunoglobulin class has a different set of functions. The following table summarizes the Physicochemical properties of each of the immunoglobulin classes and subclasses.

ods, its amino acid and corresponding gene sequences can be identified and, optionally, modified (e.g., optimized, humanized, etc.) such that the antibody can then be produced recombinantly.

For example, a specified polypeptide, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide comprises at least 8 (preferably 10, 15, 20, or 30 or more) amino acid residues of a protein's sequence and encompasses an epitope of the protein such that an antibody raised against the peptide forms a specific immune complex with the protein.

An immunogen typically is used to prepare antibodies by immunizing a suitable (i.e., immunocompetent) subject, such as a rabbit, goat, mouse, or other mammal or vertebrate. An appropriate immunogenic preparation can contain, for example, recombinantly expressed or chemically synthesized polypeptide. The preparation can further include an adjuvant, such as Freund's complete or incomplete adjuvant, or a similar immunostimulatory agent.

Antibody-producing cells can be obtained from the peripheral blood or, preferably, the spleen or lymph nodes of humans or other suitable animals that have been immunized with the immunogen of interest. Any other suitable host cell can also be used for expressing heterologous or endogenous nucleic acid encoding an antibody, specified fragment or variant thereof. The fused cells (hybridomas) or recombinant

| Property | IgG1 | IgG2 | IgG3 | IgG4 | IgM | IgA1 | IgA2 | SIgA | IgD | IgE |
|---|---|---|---|---|---|---|---|---|---|---|
| Heavy Chain | γ1 | γ1 | γ1 | γ1 | μ | α1 | α2 | α1α2 | δ | ε |
| Mean Serum conc. (mg/ml) | 9 | 3 | 1 | 0.5 | 1.5 | 3.0 | 0.5 | 0.05 | 0.03 | 0.00005 |
| Sedimentation constant | 7s | 7s | 7s | 7s | 19s | 7s | 7s | 11s | 7s | 8s |
| Mol. Wt. ($\times 10^3$) | 146 | 146 | 170 | 146 | 970 | 160 | 160 | 385 | 184 | 188 |
| Half Life (days) | 21 | 20 | 7 | 21 | 10 | 6 | 6 | ? | 3 | 2 |
| % intravascular distribution | 45 | 45 | 45 | 45 | 80 | 42 | 42 | Trace | 75 | 50 |
| Carbohydrate (%) | 2-3 | 2-3 | 2-3 | 2-3 | 12 | 7-11 | 7-11 | 7-11 | 9-14 | 12 |

The following table summarizes non-limiting examples of antibody effector functions for human antibody classes and subclasses.

| Effector function | IgG1 | IgG2 | IgG3 | IgG4 | IgM | IgA | IgD | IgE |
|---|---|---|---|---|---|---|---|---|
| Complement fixation | + | +/− | ++ | − | ++ | − | − | − |
| Placental transfer | + | +/− | + | + | − | − | − | − |
| Binding to Staph A | +++ | +++ | − | +++ | − | − | − | − |
| Binding to Strep G | +++ | +++ | +++ | +++ | − | − | − | − |

+++ = very high;
++ = high;
+ = moderate;
+/− = minimal;
− = none;
? = questionable As described below, various methods exist to produce antibodies. Once an antibody is produced by any of these meth-cells can be isolated using selective culture conditions or other suitable known methods, and cloned by limiting dilution or cell sorting, or other known methods. Cells that produce antibodies with the desired specificity can be selected by a suitable assay (e.g., ELISA).

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAH, NIH 3T3, HL-60, MLA 144, NAMALWA, NEURO 2A, or the like), or heteromyelomas, fusion products thereof, or any cell or fusion cell derived therefrom, or any other suitable cell line as known in the art (see, e.g., www.atcc.org, www.lifetech.com, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Other suitable methods of producing or isolating antibodies of the requisite specificity can be used, including, but not limited to, methods that select recombinant antibody from a peptide or polypeptide library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; Bioinvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350, 260(May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (Bioinvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or polypeptides—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., at the following web sites: www.ncbi.nlm.nih.gov/entrez/query.fcgi; www.atcc.org/phage/hdb.html; www.sciquest.com/; www.abcam.com/; www.antibodyresource.com/onlinecomp.html; www.public.iastate. edu/~pedro/research_tools.html; www.mgen.uni-heidelberg.de/SD/IT/IT.html; www.whfreeman.com/immunology/CH05/kuby05.htm; www.library.thinkquest.org/12429/Immune/Antibody.html; www.hhmi.org/grants/lectures/1996/vlab/; www.path.cam.ac.uk/~mrc7/mikeimages.html; www.antibodyresource.com/; mcb.harvard.edu/BioLinks/Immunology.html. www.immunologylink.com/; pathbox.wustl.edu/~hcenter/index.html; www.biotech.ufl.edu/~hcl/; www.pebio.com/pa/340913/340913.html; www.nal.usda.gov/awic/pubs/antibody/; www.m.ehime-u.ac.jp/~yasuhito/Elisa.html; www.biodesign.com/table.asp; www.icnet.uk/axp/facs/davies/links.html; www.biotech.ufl.edu/~fccl/protocol.html; www.isac-net.org/sites_geo.html; aximtl.imt.uni-marburg.de/~rek/AEPStart.html; baserv.uci.kun.nl/~jraats/links1.html; www.recab.uni-hd.de/immuno.bme.nwu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/~martin/abs/index.html; antibody.bath.ac.uk/; abgen.cvm.tamu.edu/lab/www.abgen.html; www.unizh.ch/~honegger/AHOseminar/Slide01.html; www.cryst.bbk.ac.uk/~ubcg07s/; www.nimr.mrc.ac.uk/CC/ccaewg/ccaewg.htm; www.path.cam.ac.uk/~mrc7/humanisation/TAHHP.html; www.ibt.unam.mx/vinstructure/stat_aim.html; www.biosci.missouri.edu/smithgp/index.html; www.cryst.bioc.cam.ac.uk/~fmolina/Web-pages/Pept/spottech.html; www.jerini.de/fr_products.htm; www.patents.ibm.com/ibm.html.Kabat et al., Sequences of Polypeptides of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to, those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323; 5,976, 862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567; PCT/: US98/16280; US96/18978; US91/09630; US91/05939; US94/01234; GB89/01334; GB91/01134; GB92/01755; WO90/14443; WO90/14424; and WO90/14430; EP 229246; each entirely incorporated herein by reference, including references cited therein.

Antibodies can also be optionally generated by immunization of a transgenic animal (e.g., mouse, rat, hamster, non-human primate, and the like) capable of producing a repertoire of human antibodies, as described herein and/or as known in the art. Cells that produce an antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7): 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Antibodies can also be prepared in milk by administering at least one antibody encoding nucleic acid to transgenic animals or mammals, such as goats, cows, horses, sheep, and the like, that produce antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference. Antibodies can additionally be prepared using at least one antibody encoding nucleic acid to provide transgenic plants and cultured plant cells (e.g., but not limited to, tobacco and maize) that produce such antibodies, specified portions or variants in the plant parts or in cells cultured therefrom.

The antibodies can bind antigens with a wide range of affinities ($K_D$). In a preferred embodiment, at least one human monoclonal antibody of the present invention can optionally bind its antigen with high affinity. For example, a human monoclonal antibody can bind human antigen with a $K_D$ equal to or less than about $10^{-7}$ M, such as but not limited to, 0.1-9.9 (or any range or value therein)$\times 10^{-7}$, $10^{-8}$, $10^{-9}$, $10^{-19}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W.H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

An antibody directed against a polypeptide (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Characteristics of Vectors

The inherent promoters of transfected cell lines with robust monoclonal antibody production capacity were investigated. It was unexpectedly found that good production levels, i.e., at about 300 mg/L, or 25-30 pg per cell per day on a specific productivity basis, were obtained, even with human gene promoters that are recognized by mouse transcription factors in the murine myeloma host cell.

Transfected cell lines C379B and C381B were observed to be robust producers of a human monoclonal antibody to the cytokine IL-12 (anti-IL-12 antibody or IL-12 mAb) encoded by fully human Ig HC and LC genes. The invention provides the complete DNA sequences of the HC and LC expression plasmids used to create the C379B and C381B cell lines and containing the anti-IL-12 antibody gene. The vectors and plasmids have been engineered to enable convenient one-step insertion of various antibody variable region genes. In a preferred embodiment, the vector is used in a one-step process to replace the anti-IL-12 variable region sequence with a variable region sequence encoding another monoclonal antibody of interest, for example, an antibody for a human interleukin, a growth factor, etc. Additionally, the vectors and plasmids allow for the replacement of antibody constant regions.

Figure 1B:
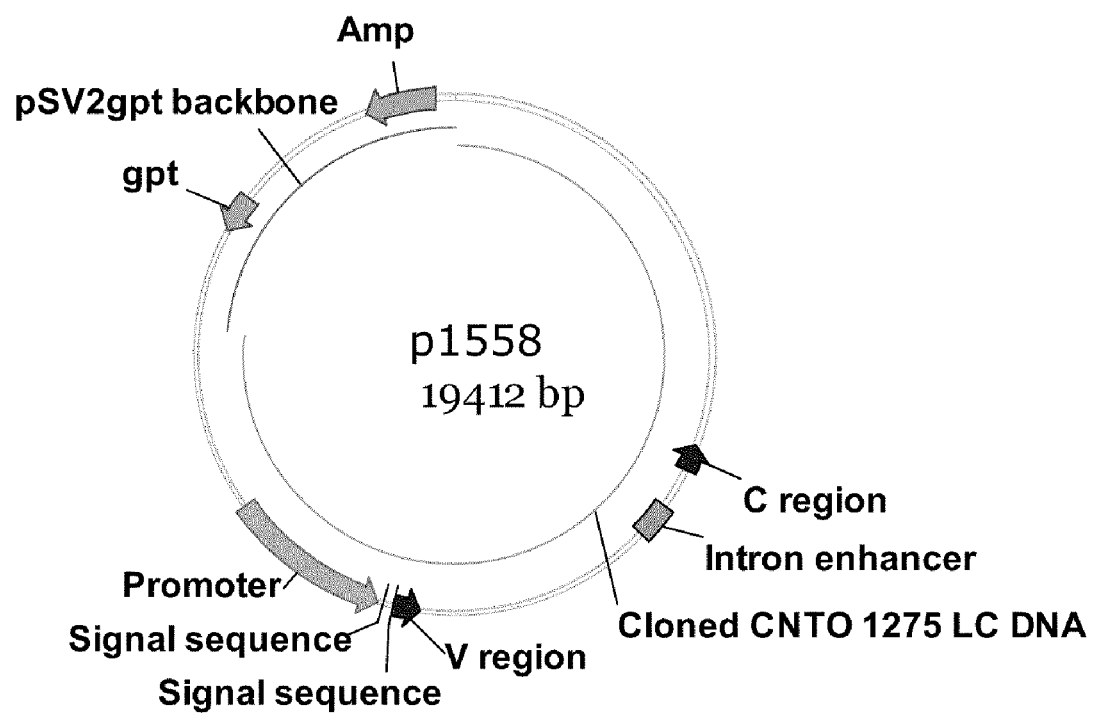
FIG. 1B is a schematic depiction of the vector map for plasmid p1558.

The maps of two expression plasmids according to the invention, p1560 and p1558, are depicted schematically in FIGS. 1A and 1B. Their sequences are disclosed in SEQ ID NOS:11 and 12. The HC plasmid specifically described herein, p1560, encodes constant regions of the human IgG1 isotype. The LC plasmid specifically described herein, p1558, encodes a constant region of the human kappa isotype. The complete DNA sequence for each of the two plasmids is around 20 kb in length and their selected features, including, without limitation, the positioning of the various expression control polynucleotide sequences, are listed in Table 1.

The antibody genes in these two plasmids are presented in reverse/complement orientation in order for the pSV2gpt vector backbones to be presented in their conventional orientation, as depicted in FIGS. 1A and 1B. Consequently, nucleotide position numbers corresponding to the carboxyl-terminal end of the antibody coding sequence (CH3 coding sequence) are lower and nucleotide position numbers corresponding to the amino-terminal end of the antibody coding sequence (V region cloning site) are higher. In addition, all antibody coding sequences correspond to the 'minus strand' as presented in the sequences shown here. This orientation is reasonable for the description of transcription factor binding sites since such binding sites may map to either the 'plus strand' or 'minus strand.'

TABLE 1

Nucleotide positions of selected features in p1560 and p1558

| Feature | p1560 | p1558 |
| --- | --- | --- |
| 5' flanking sequence | 13200-14950 | 12614-14871 |
| Ig gene promoter region | 11209-13199 | 10623-12613 |
| Signal sequence | 11060-11070 and 11154-11199 | 10422-10432 and 10559-10612 |
| V region coding sequence | 10702-11059 | 10100-10421 |
| Intron enhancer | 8449-9030 | 6765-7209 |
| CH1 coding sequence | 5002-5295 | N.A. |
| hinge coding sequence | 4566-4610 | N.A. |
| CH2 coding sequence | 4118-4447 | N.A. |
| CH3 coding sequence | 3701-4020 | N.A. |
| C kappa coding sequence | N.A. | 5943-6262 |
| gpt selectable marker | 16200-16655 | 16122-16577 |
| Amp resistance gene | 18410-19267 | 18332-19189 |

Vectors of the present invention can be used to express the constant region sequences from human IgG1, IgG2, IgG3, IgG4, IgD, IgE, or IgM, mouse IgG1, IgG2a, IgG2b, or IgG3, or rat IgG1, IgG2a, IgG2b, or IgG2c. Alternatively, vectors of the present invention can be used to express the ΔCH1 versions of the above listed constant region sequences.

Any antibody, immunoglobulin derived protein, fusion protein, other protein, or portion thereof can be substituted for the V region coding sequence in the vectors/plasmids of the present invention, e.g., extracellular domain of a TNF receptor. For such a fusion protein that includes the CH1 domain, some form of LC would be required for secretion out of the cell.

The p1560 HC expression plasmid as shown schematically herein contains the HC promoter and intron enhancer; however, the promoter and enhancer type can be varied. The p1560 HC expression plasmid contains a unique constant region coding sequence. It is an allotypic variant that encodes an Arg residue at position 214 (G1m(1,3) allotype) instead of the Lys residue (G1m(1,17) allotype).

Sequence Analysis of the HC Gene Promoter

To define elements in the promoter of the anti-IL-12 antibody HC gene that could impact gene transcription and be partially responsible for the high anti-IL-12 antibody expression levels observed in transfected cells, bioinformatic analysis of the 2000-base sequence upstream of the HC translation start codon was performed. This analysis identified sequence motifs recognized by relevant transcription factors (TFs). The most up-to-date TF database, TRANSFAC 7.2 (Matys et al, 2003), was used for the comparison. Then, various matrix and pattern search algorithms were applied to identify relevant sequences. Some of the results were subsequently validated by the relevant literature supporting the conclusion that the synergy and the combination of these TFs may drive high production of antibodies.

Several high-quality, mouse-specific transcription factor models were built with different parameters for a matrix search (Goessling et al., 2001). A mouse lymphocyte transcription factor specific model was also constructed for a matrix search. Additionally, several patch searches for different subsequence lengths (6 bps and above) were performed.

Based on these results, 21 potential binding sites for mouse TFs were identified (Table 2). Most of these TFs were B lymphocyte-specific. Some of the TFs may be activated during different stages of B cell development. Their activations are also dependent on the presence of other binding sites and the interaction of other factors.

The TRANSFAC database accession codes for these mouse TFs are: T00032 for Ap1; T01575 for STATx; T00111 for c-Ets-1; T01852 for HMG_IY; T00479 for Lyf-1; T00278 for YY1; T00613 for NF-Y; T00989 for CREB; T00402 for IRF; T02057 for IPF1; T00422 for IRF-1; T01432 for cMaf; T00814 for TFE3-S; T00017 for C/EBPBeta; T01114 for C/EBPdelta; T01864 for POU2F2/Oct-2; T00644 for POU2F1a/Oct-1; T00651 for POU5F1/Oct-3; T00702 for PU.1; T00169 for c-Rel; and T01159 for TFIID.

Six TFs were found to be located 500 bp upstream of the transcription initiation site. These are mouse POU2F2/Oct-2, POU2F1a/Oct-1, POU5F1/Oct-3, PU.1, c-Rel, and TFIID. The following auxiliary TFs or TFs in association with enhancer functions were identified: Ap1; STATx; c-Ets-1; HMG_IY; Lyf-1; YY1 and TFIID.

TABLE 2

Sequence motifs in p1560 promoter relevant to transcription

| F | Position in p1560 | Binding site ID | Sequence recognized by TF (SEQ ID NO) | Core score | Matrix/ patch | Sources/Search method | Annotation |
| --- | --- | --- | --- | --- | --- | --- | --- |
| AP-1 | 12292- | V$AP1_Q4 | agTGACTgacg (13) | 1 | 0.984 | HQ_mus/ Immuo/Patch | Interactive with c-ETs-1 and NF-Atp |
| STATx | 12643- | V$STAT_0 1 | TTCCCtgaa (14) | 1 | 0.969 | HQ_mus | Expressed in B cell, particularly in germinal center (Henderson, 1998) |
| c-Ets-1 | 12697- | V$ETS1_B | gcAGGAAgtgaaagt (15) | 1 | 0.964 | HQ_mus/ Immuo/Patch | Accelerated B cell development from proB to plasma cell |

TABLE 2-continued

Sequence motifs in p1560 promoter relevant to transcription

| F | Position in p1560 | Binding site ID | Sequence recognized by TF (SEQ ID NO) | Core score | Matrix/ patch | Sources/Search method | Annotation |
|---|---|---|---|---|---|---|---|
| HMG_1Y | 12381- | V$HMGIY_06 | GGAAAgt (16) | 1 | 0.979 | ImmuoSpecific | Auxiliary factor for other transcript-ion factors such as NF-kB or ATF-2 |
| Lyf-1 | 12239- | V$LYF1_01 | TtTGGGAgg (17) | 1 | 0.989 | ImmuoSpecific | Expressed from proB to plasma cell |
| YY1 | 11788- | V$YY1_Q6 | CaaaATGGC (18) | 1 | 0.997 | ImmuoSpecific | Ubiquitous repressor |
| NF-Y | 12311- | V$NFY_Q6_01 | agttagCCAATgg (19) | 1 | 0.974 | HQ_mus | Binds to Y box elements of MHC class II genes |
| CREB | 12289- | V$CREB_01 | TGACGtag (20) | 1 | 0.971 | HQ_mus | Expressed in lymphocytes; mediates cAMP response |
| IRF/ICSBP | 11955-; 12694- | V$IRF_Q6 | aaaaaTGAAAgaact; (21) ggaagTGAAAgtaat (22) | 1 | 0.967 | HQ_mus | Expressed in spleen and thymus. Induced by IFN-gamma |
| IPF1 | 12058- | V$IPF1_Q4 | gtgcTAATGaaa (23) | 1 | 0.965 | HQ_mus | Pancreas beta cells; in-sulin promoter factor 1 |
| IRF-1/IRF-2 | 11960+ | MOUSE$COX2_02 | TTTCATTTTT (24) | 0 | 100 | Patch | Required for B lympho-poiesis; interactive with ICSBP |
| c-Maf | 12833+; 11862- | MOUSE$IL4_02 | TCAGCA (25) | 0 | 100 | Patch | Expressed in Th2- cell, involved in Th2- specific gene activation |
| TFE3-S | 13105+ | MOUSE$IGH_10 | CATGTG (26) | 0 | 100 | Patch | Expressed from proB to plasma cells |
| C/EBP Beta | 12868+ | MOUSE$INOS_06 | TGATGTAAT (27) | 0 | 100 | Patch | Expressed from GC B cells to plasma cells; synergizes with NF-kB/rel |
| C/EBP Delta | 11886- | V$CEBPDELTA_Q6 | ggtgcaGCAATg (28) | 1 | 0.965 | HQ_mus/immuo | Expressed ubiquitously; syngergizes with NF-kB |
| PU.1 | 11506+; 12280- | MOUSE$GSHPX1_01 | CTTCTC (29) | 0 | 100 | Patch | Expressed from progenitor to GC B; no B cells if PU.1 deficient |
| POU2F2/Oct-2 | 11304+ | MOUSE$IGH_44 | ATTTGCAT (30) | 0 | 100 | Patch | Expressed from proB to plasma cells; defect in secretion if deficient |
| TFIID | 11601+; | MOUSE$MBP_04 | TTCAAA (31) | 0 | 100 | Patch | Interactive with PU.1, REL |
| c-Rel | 11580-; | V$CREL_01 | TggccTTTCC (32) | 1 | 0.968 | HQ_mus | Prevail in mature B cells, potent activator |
| POU5F1/Oct-3 | 11304+ | MOUSE$IGH_45 | ATTTGCAT (33) | 0 | 100 | Patch | May have repression function of IgH enhancer |
| POU2F1a/Oct-1 | 11303-; 12598- | V$OCT1_B | tATGCAaatg (34); ccgaaTATGCaattc (35) | 1 | 1 | HQ_mus/Patch | DNA-binding is reduced by GR in a ligand-dependent manner |

Position in HC vector in p1560 corresponds to the first nucleotide; '+' indicates plus strand; '-' indicates minus strand.
Binding site ID is the TF binding site identification assigned by TRANSFAC database.
Core score indicates core binding score calculated by TRANSFAC for the five most conserved, consecutive nucleotides used in a matrix. Score is from 0 to 1, with 1 being the best score. For patch search the core score is 0.
Match/patch score indicates the similarity of a subsequence to a matrix of TRANSFAC. Score is from 0 to 1, with 1 being the best match. If the score is 100, it was a Patch search.
Source/Search method indicates whether immuno-cell specific matrix model, high quality matrix model, and/or patch search method used.
The Oct-2 subsequence was published by Henderson et al., 1995.

Sequence Analysis of the LC Gene Promoter

The LC gene promoter region was analyzed by the same methods, which yielded a list of 20 potential mouse transcription factors and their binding sites (shown in Table 3). The TRANSFAC database accession codes for these TFs are: T02057 for IPF1, T01786 for E12, T00169 for c-Rel, T00549 for NF-AT, T01675 for NKx2-5, T01575 for STATx, T01852 for HMGIY, T00111 for c-Ets-1, T00702 for PU.1, T00278 for YY1, T00032 for Ap1, T01429 for Sox-5, T00017 for C/EBPBeta, T00814 for TF3-S, T01554 for Mitf, T01159 for TFIID, T00613 for NF-Y, T01114 for C/EBPdelta, T01864 for POU2F2/Oct-2, and T00644 for POU2F1a/Oct-1. Among them, NF-AT, C/EBPdelta, POU2F1a/Oct-1, Sox-5, E12, Statx, NF-Y, TFE3-S, Mitf, C/EBPbeta, TFIID, and POU2F were found to be located in the 500 bps upstream of the transcription start site. Light chain auxiliary TFs were Ap1, STATx, c-ETS-1, HMGIY, YY1, and TFIID.

TABLE 3

Sequence motifs in p1558 promoter relevant to transcription

| TF | Position in p1558 | Binding site ID | Sequence recognized by TF (SEQ ID NO) | Core score | Matrix/ patch | Sources/ Search method | Annotation |
| --- | --- | --- | --- | --- | --- | --- | --- |
| HMGIY | 11827- | V$HMGIY_Q6 | aaTTTCC (36) | 1 | 1.00 | ImmunoSpec | Auxiliary factor for other TF such as NF-kB or ATF-2 |
| NF-AT | 12249- | V$NFAT_06 | gctTTTCCtaaa (37) | 1 | 0.983 | ImmunoSpec | Activated T cells; composed of an AP-1 and Rel-like component |
| PU.1 | 11676- | V$PU1_Q6 | CTTCCcct (38) | 1 | 0.969 | ImmunoSpec | Expressed from progenitor to GC B cells. No B cells if deficient |
| C/EBP delta | 10913- | V$CEBP DELTA_Q6 | cATTGCtccatc (39) | 1 | 0.966 | HQ_mus/ ImmunoSpec | Expressed ubiquitously; acts synergistically with NF-kB |
| POU2F1a/ Oct-1 | 10696- | V$OCT1_Q6 | ctcaTTTGCatgttc (40) | 1 | 0.994 | HQ_mus/Patch | DNA-binding is reduced by GR in a ligand-dependent manner |
| Sox-5 | 11090- | V$SOX5_01 | ggaACAATgt (41) | 1 | 0.992 | HQ_mus/Patch | Post-meiotic germ cells; SRY-related HMG-box gene 5 |
| Nkx2-5 | 11937- | V$NKX25_01 | ttAAGTG (42) | 1 | 0.986 | HQ_mus | Expressed in lymph node stroma; TSL-1 transcriptional activator |
| c-Rel | 12253- | V$CREL_01 | gggctTTTCC (43) | 1 | 0.979 | HQ_mus | Prevail in mature B cells; potent activator |
| E12 | 10781-; 12363- | V$E12_Q6 | gaCAGGTgggg (44); ggCAGGTgggt (45) | 1 | 0.976 | HQ_mus/Patch | Functional redundancy of E2A and E2-2, except in mature B cells |
| STATx | 10857- | V$STAT_01 | TTCCCataa (46) | 1 | 0.972 | HQ_mus | Expressed in B cells, particularly in germinal centers (Henderson, 1998) |
| IPF1 | 12530- | V$IPF1_Q4 | tatCATTAaggc (47) | 1 | 0.960 | Patch | Pancreas beta-cells; insulin promoter factor 1 |
| NF-Y | 10929- | V$NFY_Q6_01 | catacaCCAATga (48) | 1 | 0.966 | HQ_mus | Binds to Y-box elements of MHC-class II genes |
| TFE3-S | 11133- | MOUSE$ IGH_10 | CATGTG (49) | 0 | 100 | Patch | Expressed from pro-B to plasma cells |

TABLE 3-continued

Sequence motifs in p1558 promoter relevant to transcription

| TF | Position in p1558 | Binding site ID | Sequence recognized by TF (SEQ ID NO) | Core score | Matrix/ patch | Sources/ Search method | Annotation |
|---|---|---|---|---|---|---|---|
| Mitf | 11133- | MOUSE$ TBX2_01 | CATGTG (50) | 0 | 100 | Patch | Melanocyte cell; forms heterodimers with TFE3-related proteins |
| Ap-1 | 11163+; 12025+; 12092+ | MOUSE$IL 2_11 | AGGTAAT (51) | 0 | 100 | Patch | Interacts with c-Ets-1 or NF-Atp |
| C/EBP beta | 11065- | V$CEBPB_02 | aaatgtTGCAAgta (52) | 1 | 0.917 | ImmunoSpec | Expressed from germincal center B cells to plasma cells |
| YY1 | 11564- | MOUSE$ CMYC_05 | ACATGG (53) | 0 | 100 | Patch | Ubiquitous repressor |
| c-Ets-1 | 11792- | MOUSE$ TIMP1_02 | CAGGAAG (54) | 0 | 100 | Patch | Accelerated B-cell development from pro-B to plasma cells |
| TFIID | 10891-; 11015+ | MOUSE$ MBP_04 | TTCAAA (55) | 0 | 100 | Patch | Interactive-with PU.1 and REL |
| POU2F2/ Oct-2 | 10700- | MOUSE$ IGH_44 | ATTTGCAT (56) | 0 | 100 | Patch | Expressed from pro-B to plasma cell. Defective secretion if deficient |

Position in LC vector p1558 corresponds to the first nucleotide; '+' indicates plus strand; '-' indicates minus strand.

Summary of Vector Properties

The unique HC and LC promoters described here have been shown to be capable of driving high levels of gene expression, as in the case of the C379B and C381B transfected cell lines. The identification of sequence motifs that can determine transcriptional levels provides information to enhance gene transcription by customizing promoter and enhancer sequences and using host cells that express the best combination of transcription factors for these promoters. This could include using a host cell that has been modified to overexpress transcription factors that can enhance expression and/or a host cell that has been modified to underexpress transcription factors that may impede expression, among others. For example, host cells can be co-transfected with a gene encoding OBF-1 transcription factor to obtain higher OBF-1 levels, or using anti-sense, interfering RNA (e.g., siRNA or shRNA), or gene knockout approaches to reduce expression of TFs that may negatively regulate Ig gene transcription, e.g. NF-μNR.

The present invention also comprises methods of identifying the interaction between the sequences of promoter and enhancer regions and transcription factors in vectors/plasmids and cellular hosts, moderating the interaction by altering the sequences to effect transcription, translation, and gene expression levels, and determining the modifications and adjusting in order to control the levels. The sequence alteration may be by mutations to the sequences in the regions or by complete replacement of the regions compatible with the cell line used.

EXAMPLES

The following specific examples are intended to illustrate the invention and should not be construed as limiting the scope of the claim.

Example 1

Cloning of Human Anti-Human Interleukin-12 Antibody Genes and Preparation of High-Producing Cell Lines Summary The C340A hybridoma cell line that secretes the human anti-human IL-12 mAb produces less than 0.4 μg/ml of spent cell culture. This level of production was insufficient to generate the large amounts of material needed for future studies. To increase the level of IL-12 mAb production and to have a well characterized cell line as the source, the IL-12 mAb heavy and light chain genes were cloned and introduced into P3X63Ag8.653 (653) or SP2/0-Ag14 (SP2/0) mouse myeloma cells. The IL-12 mAb heavy and light chain genes were cloned from a bacteriophage library prepared from C340A hybridoma genomic DNA and transferred into plasmid vectors. The resulting heavy and light chain expression plasmids were then sequenced and the sequences compared to known germline sequences. These plasmids were introduced into mouse myeloma cells and transfected clones were screened for human IgG expression by ELISA to identify the highest producers. Selected parental clones were then subcloned to identify higher producing and homogeneous clones. Subclones of interest were then characterized by growth curve analysis and tested for stability of mAb production over time. An antigen binding assay performed with supernatants from these cell lines showed that the recombinant mAb bound to immobilized human interleukin 12 (huIL-12) with an affinity indistinguishable from purified antibody from the original C340 hybridoma, confirming that the genes which were cloned and expressed were the IL-12 mAb encoding genes. The highest producing subclones in spent T flask cultures were 653 transfectant C379B which produced 135 µg/ml of IL-12 mAb and SP2/0 transfectant C381B which produced 150 µg/ml of IL-12 mAb.

Materials

Trisol was obtained from Gibco BRL, Grand Island, N.Y. Proteinase K was from Sigma Chemical, St. Louis, Mo. Restriction enzymes were purchased from New England Biolabs, Beverly, Mass. The Lambda EMBL3/Gigapack III Gold Cloning Kit was from Stratagene, La Jolla, Calif. Protran membranes were supplied by Schleicher & Schuell, Keene, N.H. RNAse and the Random Prime Labeling Kit were from Boehringer Mannheim, Germany. DNAse was from Pharmacia, Uppsala, Sweden. α-$^{32}$P-dCTP was purchased from DuPont NEN, Boston, Mass. Human IL-12 was purchased from RDI Immunochemicals, Flanders, N.J. Custom oligonucleotides were purchased from Biosource International, Camarillo, Calif. The names, sequence identification numbers, and sequences of the oligonucleotides used in this work are as follows:

| Name   | SEQ ID | Sequence              |
|--------|--------|-----------------------|
| 5'-10  | 1      | CCCAGGTGCAGCTGGTG     |
| 5'-46  | 2      | CTCAGGTGCAGCTGGTGG    |
| 5'-63  | 3      | CCCAGGTGCAGCTACAG     |
| 5'-73  | 4      | CCGAGGTGCAGCTGGTG     |
| huJH4  | 5      | AACCTCGAGTTAACGGAGG   |
| huJH6  | 6      | GCAGGAAACCCCACAGG     |
| 5'VK1  | 7      | ATCCAGATGACCCAGTCT    |
| 5'VK2  | 8      | ATCGTGTTGACACAGTCTCCA |
| huJK3  | 9      | AATATGCACAAAACTTGCAC  |
| huJK5  | 10     | ATTTGAGCCTCTAAAGGTC   |

Cloning of the IL-12 mAb Heavy and Light Chain Genes

To clone and isolate the IL-12 mAb, heavy and light chain genes from C340 hybridoma DNA, a genomic library was first prepared. Total genomic DNA was isolated from $5\times10^7$ cells by digestion with 0.1 mg/ml proteinase K in a buffer containing 100 mM NaCl, 10 mM Tris-Cl (pH 8.0), 25 mM EDTA (pH 8.0) and 0.5% SDS, and subsequent phenol/chloroform extraction and ethanol precipitation. Two hundred µgs of C340 genomic DNA were then digested with 8 units/ml Sau3A restriction enzyme and aliquots were taken every 5 minutes. Based on the analysis of fragment sizes by agarose gel electrophoresis, the 5, 10 and 15 minute aliquots, which showed the desired partial digestion, were pooled. These aliquots were loaded onto a 10% to 40% sucrose gradient and spun at 22,000 RPM for 42 hours in a Beckman ultracentrifuge (SW41TI rotor) to fractionate the fragments by size. Five hundred µl fractions were collected and then analyzed on an agarose gel to visualize the DNA fragments. DNA was isolated from fractions which contained fragments in the size range of 15-23 kb. The purified genomic DNA fragments were ligated into the Lambda EMBL3 bacteriophage vector and packaged into bacteriophage particles using the Lambda EMBL3/Gigapack III Gold Cloning Kit according to the manufacturer's protocol. The final genomic library consisted of approximately 1 million clones.

To screen the genomic library for the IL-12 mAb heavy and light chain genes, 640,000 bacteriophage from the Sau3A library were mixed with *E. coli* strain Y1090r- and plated onto sixteen 150 mm agar plates at a density of 40,000 clones per plate. Bacteriophage DNA from all 16 plates was transferred onto two sets of Protran nitrocellulose membranes. Briefly, nitrocellulose membranes were laid onto the plates, left for 2 minutes, removed and sequentially treated with denaturation solution, neutralization solution, and Tris buffer as described in the Lambda EMBL3/Gigapack III Gold Cloning Kit instruction manual. A Stragene UV crosslinker was used to fix the denatured DNA onto the membranes.

Probes for the heavy and light chains were prepared using genomic DNA fragments that contained either human IgG1 heavy chain constant region sequences (2.8 kb EcoRI/HindIII fragment from p747) or human kappa light chain constant region sequences (2.4 kb NcoI/Xba fragment from p95). Both probes were labeled with α-$^{32}$P-dCTP using a Random Primed DNA Labeling Kit.

Nitrocellulose membranes were prehybridized for one hour in hybridization buffer (50% formamide, 5×SSC, 3.75 mM Tris pH 7.8, 1×Denhardts Solution, 25 µg/ml sheared DNA and 5% dextran sulfate). Probes with a CPM of approximately $1\times10^8$ were denatured at 100° C. then added to the hybridization buffer and allowed to hybridize at 42° C. overnight. Filters were washed twice in 2×SSC, 0.1% SDS for 10 minutes at RT, then twice in 0.2×SSC, 0.1% SDS at 65° C. with shaking. Filters were dried and exposed to x-ray film.

Autoradiographic signals corresponding to thirteen heavy chain and nine light chain bacteriophage clones were detected. To isolate these bacteriophage clones, a plug of agarose was collected from the area corresponding to each positive signal using the large end of a Pasteur pipette and transferred into a tube containing 500 µls of lambda dilution buffer and 20 µls of chloroform. To purify the bacteriophage clones to homogeneity, the bacteriophage isolates were replated at 1000-3000 pfu/plate and a secondary round of screening was performed. From the secondary screening, the four most distinct positives for both the heavy and light chain were chosen for a third round of screening. For the third and final round of screening phage isolates were titered as before and then plated at 100 pfu/plate. Two plaques were picked for each positive clone and the purified bacteriophage clones were stored in lambda dilution buffer with chloroform at 4° C.

Preparation of IL-12 mAb Expression Plasmids

In order to characterize the cloned DNA inserts, DNA was purified from the positive bacteriophage clones using a liquid culture method. Two hundred µl of Y1090r-bacterial culture was combined with 100 µl of bacteriophage in 1× lambda dilution buffer and the mixture was incubated at 37° C. for 15 minutes to allow the bacteriophage to bind the bacteria. Then, 10 ml of LB media containing 10 mM MgSO$_4$ was added and the cultures incubated overnight at 37° C. with shaking. The next day 100 µl of chloroform was added to each tube to completely lyse the bacteria. After clarification, 20 µg of RNAse and 20 µg of DNAse were added and the samples incubated at 37° C. for 30 minutes. To precipitate the phage particles, 20 ml of a solution containing 20% PEG and 2.5 M NaCl was then added and the samples incubated on ice for 1.5 hours. The bacteriophage particles were pelleted and then washed once with 1× lambda dilution buffer. The pellet was then resuspended in a solution of 0.2% SDS and 20 mM EDTA and incubated at 68EC for 15 minutes. The DNA was extracted from the bacteriophage particles using phenol and chloroform, and then the DNA was precipitated with isopropanol and washed with 70% ethanol. The purified DNA was resuspended in 50 µl of TE buffer.

PCR was used to determine which, if any, of the clones contained human variable regions in addition to the constant region known to be present based on homology to the radiolabeled probes. Because the sequence of the variable regions at the 5' ends was unknown, primers were pooled and used to prime the sequencing reactions. For the HC reactions, a mix of four primers, 5'-10, 5'-46, 5'-63, and 5'-73, representing each of the possible sequences was used. At the 3' end, primers huJH4 and huJH6 which are homologus to either the JH4 or JH6 regions were used. For the LC, at the 5' end, a mixture of two consensus primers 5'VK1 and 5'VK2 was used. At the 3' end, primers huJK3 or huJK5 homologous to the JK3 or JK5 regions were used. Standard 100 µl PCR reactions were performed using 0.5 nanograms of phage DNA as template. Primers were annealed at 48° C. and 25 cycles of PCR were performed. Reactions were fractionated on an agarose gel for visualization.

To transfer the cloned inserts from the bacteriophage vector to a plasmid that contains the gpt selectable marker gene, bacteriophage DNA from clones containing both the variable and constant regions were digested with SalI. The resulting fragments were purified and cloned between the XhoI and SalI sites of plasmid p1351. Because there was an internal SalI site in the heavy chain variable region coding sequence, two SalI fragments that were 13 kb and 4 kb in size had to be transferred into the p1351 expression vector sequentially. First the 13 kb SalI fragment was cloned into the XhoI and SalI sites of p1351 and the resulting plasmid designated p1557. Subsequently, the 4 kb fragment was transferred into p1557 and the resulting final expression plasmid was termed p1560. The 15 kb light chain SalI insert was able to be transferred in one step and the final expression plasmid was designated p1558.

Cell Transfections, Screening for High Producers and Expression of the Cloned Genes Heavy chain plasmid p1560 was linearized by digestion with PvuI restriction enzyme and light chain plasmid p1558 was linearized using SalI restriction enzyme. 653 and SP2/0 cells were separately transfected with the premixed linearized plasmids by electroporation and cells cultured and transfectants selected using mycophenolic acid as described. Cell supernatants from mycophenolic acid-resistant colonies were assayed approximately two weeks later for human IgG. For this experiment, cell supernatants were incubated on 96-well ELISA plates that had been previously coated with goat anti-human IgG Fc-specific antibodies. Bound human IgG was detected using alkaline phosphatase-conjugated goat anti-human IgG (H+L) antibody and alkaline phosphatase substrates as described. Cells of the higher producing clones were transferred to 24-well culture dishes in standard media, IMDM, 5% FBS, 2 mM glutamine, mycophenolic acid selection mix (5 g/L Xanthene, 250 mg/L Hypoxanthene, 50 mg/L Mycophenolic acid, 50 mM NaOH). Supernatants later collected from spent cultures were carefully quantitated by ELISA by doing serial two-fold dilutions of each sample and comparing the O.D. values to a standard curve prepared using purified mAb from C340 cells. Selected clones were then transferred to T75 flasks and the production of human IgG similarly quantitated by ELISA. Based on these values, the highest producing transfectants were subcloned by seeding an average of one cell per well and performing ELISA assays of cell supernatants from individual subclone colonies.

The subclones selected for final analyses were the 653 transfectant C379B and the SP2/0 transfectants C381B. Maximal production levels for C379B and C381B were 135 µg/ml and 150 µg/ml, respectively. Peak cell densities for C379B and C381B were $1 \times 10^6$ cells/ml and $1.45 \times 10^6$ cells/ml, respectively.

Assay for IL-12 Binding

Cell supernatants from three parental lines (653 transfectants clone 2 and clone 18 and SP2/0 transfectant clone 1) were used to test the antigen binding characteristics of the recombinant anti-huIL-12 mAb. The concentrations of mAb in the three cell supernatant samples were first determined by ELISA. Titrating amounts of the supernatant samples, or purified mAb from C340 cells as a positive control, were then incubated in 96-well plates that had been previously coated with 2 µg/ml of huIL-12. Bound mAb was then detected with alkaline phosphatase-conjugated goat anti-human IgG (H+L) antibody and the appropriate alkaline phosphatase substrates.

The antigen binding characteristics of supernatants from three separate parental cell lines were compared to mAb purified from C340 cells. It was shown that mAb from transfected cell supernatants bound specifically to immobilized huIL-12 in a manner indistinguishable from mAb purified from the original C340 cell line. This result confirmed that the correct genes were cloned and expressed.

Sequencing

The sequences of the light chain and heavy chain expression plasmid inserts were determined using BigDye terminator chemistry and an ABI377 automated DNA sequencer. Primers were designed to sequence either upstream or downstream from known sequences in the variable region, constant region, and vector backbone. Each sequencing reaction gave approximately 500 bp of additional sequence which was aligned using the AssemblyLIGN program. Following each round of sequencing, primers were designed to continue sequencing upstream and downstream of the known sequence. The sequences of p1558 and p1560 are shown in SEQ ID NO:11 and 12.

The cloned insert containing the IL-12 mAb light chain coding sequences is approximately 15 kb in length. The start codon is located 4310 base pairs from the 5' end of the insert. There is a 3838 bp J-C intron between the variable and constant region coding sequences and approximately 6 kb of noncoding sequence downstream of the constant region. The light chain constant region is the Km(3) allotype, the same as cA2 and 7E3.

The cloned insert containing the IL-12 mAb heavy chain coding sequences is approximately 16 kb in length. The start codon is located 4802 bp from the 5' end of the insert. There is a 5406 bp J-C intron and approximately 4.8 kb of noncoding sequence downstream of the constant region. The IgG allotype is G1m(f), defined by the arginine (arg) at position 214. This is different than cA2 which has a lysine (lys) at position 214 and is therefore of the G1m(z) allotype.

Although illustrated and described above with reference to certain specific embodiments, the present invention is nevertheless not intended to be limited to the details shown. Rather, the present invention is directed to an expression vector or plasmid having various sequences, apparatus, and kits disclosed herein and uses thereof, and various modifications may be made in the details within the scope and range of equivalents of the claims and without departing from the spirit of the invention.

What is claimed:

1. An expression vector comprising the nucleic acid sequence of SEQ ID NO:12.

2. A host cell comprising the expression vector of claim 1.

3. The host cell of claim 2, wherein the host cell is a mammalian host cell.

4. The host cell of claim 3 wherein the host cell is a murine myeloma host cell.

\* \* \* \* \*